United States Patent [19]
Lewis et al.

[11] Patent Number: 6,124,281
[45] Date of Patent: Sep. 26, 2000

[54] AZOLOBENZAZEPINE DERIVATIVES AS NEUROLOGICALLY ACTIVE AGENTS

[75] Inventors: Joseph James Lewis; Kelly Anne Brush; Laura Enid Garcia-Davenport; William Jackson Frazee; Marc Jerome Chapdelaine, all of Wilmington, Del.

[73] Assignee: Zeneca Limited, United Kingdom

[21] Appl. No.: 09/142,221

[22] PCT Filed: Mar. 4, 1997

[86] PCT No.: PCT/GB97/00592

§ 371 Date: Sep. 3, 1998

§ 102(e) Date: Sep. 3, 1998

[87] PCT Pub. No.: WO97/32883

PCT Pub. Date: Sep. 12, 1997

Related U.S. Application Data

[60] Provisional application No. 60/013,528, Mar. 8, 1996.
[51] Int. Cl.[7] .......................... C07D 487/04; A61K 31/55
[52] U.S. Cl. .......................... 514/215; 540/521; 548/255; 548/374.1
[58] Field of Search ................................... 540/521, 522; 514/215, 217

[56] References Cited

U.S. PATENT DOCUMENTS 5,686,442  11/1997  Ohtsuka et al. .................. 514/211

FOREIGN PATENT DOCUMENTS

WO 94/29275  12/1994  WIPO.
WO 95/18130  7/1995  WIPO.
WO 97/00258  1/1997  WIPO.

*Primary Examiner*—Mark L. Berch
*Assistant Examiner*—Bruck Kifle
*Attorney, Agent, or Firm*—Kenneth F. Mitchell

[57] ABSTRACT

The invention relates to azolobenzazepine derivatives of formula (I), wherein: X is O or S; $R^1$, $R^2$, $R^3$ and $R^4$ are independently hydrogen, perfluorolower-alkyl, halogen, nitro or cyano; and C together with the carbon atoms to which it is attached forms a 5-membered aromatic heterocycle selected from the group consisting of a pyrazol and triazole, to pharmaceutical compositions containing them and to methods for the treatment of neurological disorders utilizing them.

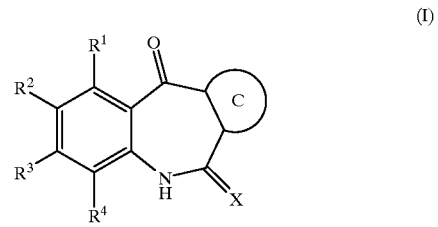

(I)

23 Claims, No Drawings

AZOLOBENZAZEPINE DERIVATIVES AS NEUROLOGICALLY ACTIVE AGENTS

This application claims the benefit of U.S. provisional application Pat. No. 60/013,528, filed Mar. 8, 1996.

Which is a National Phase of PCT Application PCT/GB97/00592 filed Mar. 4, 1997, priority of which is claimed.

The invention relates to azolobenzazepine derivatives, to pharmaceutical compositions containing the same and to the method of use thereof in the treatment of neuroloical disorders.

More specifically, the invention relates to compounds of the Formula I:

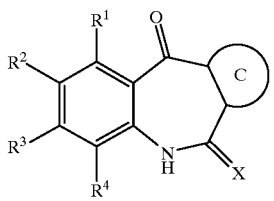

wherein:
X is O or S;
$R^1$, $R^2$, $R^3$ and $R^4$ are independently hydrogen, perfluorolower-alkyl, halogen, nitro is or cyano; and
C together with the carbon atoms to which it is attached forms a 5-membered aromatic heterocycle selected from the group consisting of:

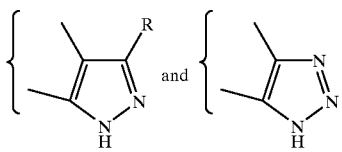

or tautomers thereof, wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, or phenyl-lower-alkylamino), —C(O)NR$^6$R$^7$ (wherein R$^6$ and R$^7$ are independently hvdrogen, phenyl, phenyl-lower-alkyl, lower-alkoxy-lower-alkyl, hydroxy-lower-alkyl, lower-alkyl, lower-alkoxy, hydroxy, or cycloalkyl, or R$^6$ and R$^7$ together with the nitrogen atom to which they are attached form a 5- or 6-membered non-aromatic heterocycle selected from the group consisting of morpholinyl, piperidinyl, piperazinyl, pyrrolidinyl and thiomorpholinyl), formyl, phenylcarbonyl, phenyl, lower-alkylcarbonyl, perfluorolower-alkyl, lower-alkoxy-carbonyl-lower-alkyl, carboxy-lower-alkyl, or phenyl-lower-alkylcarbonyl; wherein said phenyl, phenyl-lower-alkyl, phenyl-lower-alkynyl, phenyl-lower-alkyl-amino, phenylcarbonyl or phenyl-lower-alkylcarbonyl groups may optionally be substituted on the phenyl group thereof by one to three substituents, the same or different, selected from the group consisting of lower-alkyl, lower-alkoxy, halogen, hydroxy and trifluoromethyl;

or a pharmaceutically acceptable acid-addition salt of basic members thereof; or a pharmaceutically acceptable base-addition salt of acidic members thereof; with the proviso that when C together with the carbon atoms to which it is attached forms a triazole ring, at least one of R$^1$, R$^2$, R$^3$ or R$^4$ must be other than hydrogen.

The compounds of the Formula I have been found to function as antagonists of the effects which excitatory amino acids, such as glutamate, have upon the NMDA receptor complex and are thus usefull in the treatment of neurological disorders.

Compounds within the ambit of Formula I above are those wherein:

X, R$^1$, R$^2$, R$^3$, R$^4$ and C are as defined above; and
R is cyano, —C(O)OR (wherein R is hydrogen, lower-alkyl, lower-alkenyl, lower-alkynyl, cycloalkyl-lower-alkyl, phenyl, phenyl-lower-alkyl, phenyl-lower-alkynyl, lower-alkylthio- lower-alkyl, halo-lower-alkyl, trifluoromethyl-lower-alkyl, lower-alkylamino, cycloalkylamino, or phenyl-lower-alkyl-amino), —C(O)NR$^6$R$^7$ (wherein R$^6$ and R$^7$ are independently hydrogen, phenyl, phenyl-lower-alkyl, lower-alkoxy-lower-alkyl, lower-alkyl, lower-alkoxy, hydroxy or cycloalkyl, or R$^6$ and R$^7$ together with the nitrogen atom to which they are attached form a morpholinyl group), formyl, phenylcarbonyl, phenyl, lower-alkylcarbonyl, perfluorolower-alkyl, lower-alkoxy-carbonyl-lower-alkyl, or carboxy-lower-alkyl; wherein said phenyl, phenyl-lower-alkyl, phenyl-lower-alkynyl, phenyl-lower-alkylamino or phenylcarbonyl groups may optionally be substituted on the phenyl group thereof by one substituent selected from the group consisting of lower-alkyl, lower-alkoxy, halogen, hydroxy and trifluoromethyl.

Other compounds within the ambit of Formula I above are those wherein:

X, R$^1$, R$^2$, R$^3$, R$^4$ and C are as defined above: and
R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkylamino, cycloalkylamino, or phenyl-lower-alkyl amino), —C(O)NR$^6$R$^7$ (wherein R$^6$ and R$^7$ are independently hydrogen, phenyl, phenyl-lower-alkyl, lower-alkoxy-lower-alkyl, lower-alkyl, lower-alkoxy, or hydroxy, or R$^6$ and R$^7$ together with the nitrogen atom to which they are attached form a morpholinyl group), formyl, phenylcarbonyl, phenyl, perfluorolower-alkyl, lower-alkoxycarbonyl-lower-alkyl, or carboxy-lower-alkyl.

Preferred compounds of the formula I above are those wherein R$^1$, R$^2$, R$^3$ and R$^4$ are independently hydrogen or halogen; and X, C and R are as defined directly above.

Particularly preferred compounds of the Formula I above are those wherein:

X and C are as defined directly above;
R$^1$, R$^2$, R$^3$ and R$^4$ are independently hydrogen or halogen; and R is cyano, —C(O)OR$^5$ (wherein R$^5$ is hydrogen, methyl, ethyl, propyl, isopropyl, butyl, sec-butyl, isobutyl, 2-propenyl, 3-butenyl, 1-methyl-3-butenyl, 3-methyl-3-butenyl, 4-pentenyl, 3-butynyl, cyclopropylmethyl, phenyl, phenylmethyl, phenylethyl, phenylpropyl, 3-phenyl-2-propynyl, methylthioethyl, methylthiopropyl, chloroethyl, chloropropyl, 2,2,2-trifluoroethyl, isopropylamino, cyclohexylamino, tert-butyl-arnino, phenylmethylamino), —C(O)NR$^6$R$^7$ (wherein R$^6$ and R$^7$ are independently hydrogen, phenylmethyl, phenyl, methoxyethyl, ethoxyethyl, propyl, methyl, methoxy, or hydroxy, or R$^6$ and R$^7$ together with the nitrogen atom to which they are attached form a morpholinyl group), formyl, phenylcarbonyl, phenyl, trifluoromethyl, tert-butoxy-carbonylmethyl or carboxymethyl.

More particularly preferred compounds of the Formula I above are those wherein:

One of $R^1$, $R^2$, $R^3$ or $R^4$ is chloro and the others are hydrogen: and X, C and R are as defined directly above.

Preferred species of the invention include:

7-chloro-3-(carboxy)pyrazolo[3,4-c][1]benzazepine-4,10-(1H,9H)-dione, 7-chloro-3-cyanopyrazolo[3,4-c][1]benzazepine-4,10-(1H,9H)-dione, 7-chloro-3-trifluoromethylpyrazolo[3,4-c][1]benzazepine-4,10(1H,9H)-dione, 3-methoxycarbonyl-7-chloropyrazolo[3,4-c][1]benzazepine-4,10(1H,9H)-dione, 7-chloro-3-(ethoxycarbonyl)pyrazolo[3,4-c][1]benzazepine-4,10(1H,9H)-dione, 3-propoxycarbonyl-7-chloropyrazolo[3,4-c][1]benzazepine-4,10(1H,9H)-dione, 7-chloro-3-(2-propenyloxycarbonyl)pyrazolo[3,4c][1]-benzazepine-4,10(1H,9H)-dione, 7-chloro-3-(isopropoxycarbonyl)pyrazolo[3,4-c][1]-benzazepine-4,10(1H,9H)-dione, 3-butoxycarbonyl-7-chloropyrazolo[3,4c][1]benzazepine-4,10(1H,9H)-dione, 3-(3-butenyloxycarbonyl)7-chloropyrazolo[3,4-c][1]-benzazepine-4,10(1H,9H)-dione, and 3-(3-butynyloxycarbonyl)-7-chloropyrazolo[3,4-c][1]-benzazepine-4,10(1H,9H)-dione; or a pharmaceutically acceptable salt thereof.

Another group of compounds within the ambit of Formula I above are those wherein:

X is O or S;

$R^1$, $R^2$, $R^3$ and $R^4$ are independently hydrogen, perfluorolower-alkyl halogen, nitro or cyano; and C together with the carbon atoms to which it is attached forms a 5-membered aromatic heterocycle of the formula:

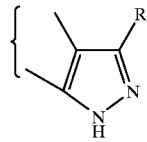

or tautomers thereof, wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, or phenyl-lower-alkylamino), —C(O)NR$^6$R$^7$ (wherein R$^6$ and R$^7$ are independently hydrogen, phenyl, phenyl-lower-alkyl, lower-alkoxy-lower-alkyl, hydroxy-lower-alkyl, lower-alkyl, lower-alkoxy, hydroxy, or cycloalkyl, or R$^6$ and R$^7$ together with the nitrogen atom to which they are attached form a 5- or 6-membered non-aromatic heterocycle selected from the group consisting of morpholinyl, piperidinyl, piperazinyl, pyrrolidinyl and thiomorpholinyl), formyl, phenylcarbonyl, phenyl, lower-alkylcarbonyl, perfluorolower-alkyl, lower-alkoxycarbonyl-lower-alkyl, carboxy-lower-alkyl, or phenyl-lower-alkylcarbonyl; wherein said phenyl, phenyl-lower-alkyl, phenyl-lower-alkynyl, phenyl-lower-alkylamino, phenylcarbonyl or phenyl-lower-alkylcarbonyl groups may optionally be substituted on the phenyl group thereof by one to three substituents, the same or different, selected from the group consisting of lower-alkyl, lower-alkoxy, halogen, hydroxy and trifluoromethyl.

Another group of compounds within the ambit of Formula I above are those wherein:

X is O or S;

$R^1$, $R^2$, $R^3$ and $R^4$ are independently hydrogen, perfluorolower-alkyl, halogen, nitro or cyano; and C together with the carbon atoms to which it is attached forms a 5-membered aromatic heterocycle of the formula:

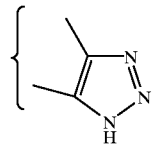

or tautomers thereof.

Preferred compounds of the Formula I within this latter group are those wherein $R^1$, $R^2$, $R^3$, $R^4$ are independently hydrogen or halogen; and X and C are as defined directly above.

Particularly preferred compounds of the Formula I within this latter group are those wherein one of $R^1$, $R^2$, $R^3$ or $R^4$ is chloro and the others are hydrogen, and X and C are defined directly above.

Preferred species within this latter group of compounds of the Formula I are:

7-chloro-1,2,3-triazolo[4,5-c][1]benzazepine-4,10(1H,9H)-dione;

6-chloro-1,2,3-triazolo[4,5-c][1]benzazepine-4,10(1H,9H)-dione; and 5-chloro-1,2,3-triazolo[4-5-c][1]benzazepine-4,10(1H,9H)-dione;

or a pharmaceutically acceptable salt thereof.

The invention fuirther relates to a method for the treatment of neurological disorders which comprises administering to a patient in need of such treatment an effective amount of a compound of the Formula I

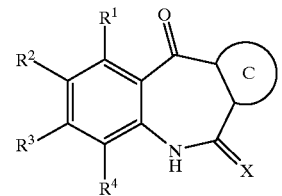

wherein:

X is O or S;

$R^1$, $R^2$, $R^3$ and $R^4$ are independently hydrogen, perfluorolower-alkyl, halogen, nitro or cyano; and C together with the carbon atoms to which it is attached forms a 5-membered aromatic heterocycle selected from the group consisting of:

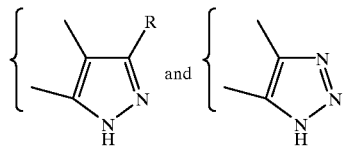

or tautomers thereof, wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, or phenyl-lower-alkylamino), —C(O)NR$^6$R$^7$ (wherein R$^6$ and R$^7$ are independently hydrogen, phenyl, phenyl-lower-alkyl, lower-alkoxy-lower-alkyl, hydroxylower-alkyl, lower-alkyl, lower-alkoxy, hydroxy, or cycloalkyl, or R$^6$ and R$^7$ together with the nitrogen atom to which they are attached form a 5- or 6-membered non-aromatic heterocycle selected from the group consisting of morpholinyl, piperidinyl, piperazinyl, pyrrolidinyl and thiomorpholinyl), formyl, phenylcarbonyl, phenyl, lower-alkylcarbonyl, perfluorolower-alkyl, lower-alkoxy-carbonyl-lower-alkyl, carboxy-lower-alkyl, or phenyl-lower-alkylcarbonyl; wherein said phenyl, phenyl-lower-alkyl, phenyl-lower-alkynyl, phenyl-lower-alkylamino, phenylcarbonyl or phenyl-lower-alkylcarbonyl groups may optionally be substituted on the phenyl group thereof by one to three substituents, the same or different, selected from the group consisting of lower-alkyl, lower-alkoxy, halogen, hydroxy and trifluoromethyl;

or a pharmaceutically acceptable acid-addition salt of basic members thereof; or a pharmaceutically acceptable base-addition salt of acidic members thereof.

The invention further relates to a pharmaceutical composition which comprises a compound of the formula I:

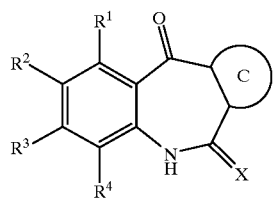

I wherein:

X is O or S;

R$^1$, R$^2$, R$^3$ and R$^4$ are independently hydrogen, perfluorolower-alkyl, halogen, nitro or cyano; and C together with the carbon atoms to which it is attached forms a 5-membered aromatic heterocycle selected from the group consisting of:

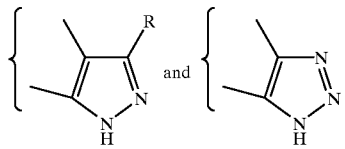

or tautomers thereof, wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, or phenyl-lower-alkylamino), —C(O)NR$^6$R$^7$ (wherein R$^6$ and R$^7$ are independently hydrogen, phenyl, phenyl-lower-alkyl, lower-alkoxy-lower-alkyl, hydroxy-lower-alkyl, lower-alkyl, lower-alkoxy, hydroxy, or cycloalkyl, or R$^6$ and R$^7$ together with the nitrogen atom to which they are attached form a 5- or 6-membered non-aromatic heterocycle selected from the group consisting of morpholinyl, piperidinyl, piperazinyl, pyrrolidinyl and thiomorpholinyl), formyl, phenylcarbonyl, phenyl, lower-alkylcarbonyl, perfluorolower-alkyl, lower-alkoxy-carbonyl-lower-alkyl, carboxy-lower-alkyl, or phenyl-lower-alkylcarbonyl; wherein said phenyl, phenyl-lower-alkyl, phenyl-lower-alkynyl, phenyl-lower-alkylamino, phenylcarbonyl or phenyl-lower-alkylcarbonyl groups may optionally be substituted on the phenyl group thereof by one to three substituents, the same or different, selected from the group consisting of lower-alkyl, lower-alkoxy, halogen, hydroxy and trifluoromethyl;

or a pharmaceutically acceptable acid-addition salt of basic members thereof; or a pharmaceutically acceptable base-addition salt of acidic members thereof; together with a pharmaceutically acceptable carrier, adjuvant, diluent or vehicle; with the proviso that when C together with the carbon atoms to which it is attached forms a triazole ring, at least one of R$^1$, R$^2$, R$^3$ or R$^4$ must be other than hydrogen.

The invention fuirther relates to a process for preparing a compound of the Formula I which comprises:

(I) treating a compound of the Formula II

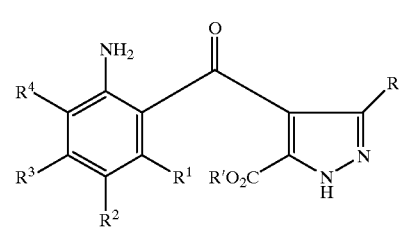

II wherein R' is lower-alkyl, with an ammonium salt, 2-hydroxypyridine, or a base to prepare a corresponding compound of the formula I wherein C is a pyrazole ring; or (2) treating a compound of the formula XIII

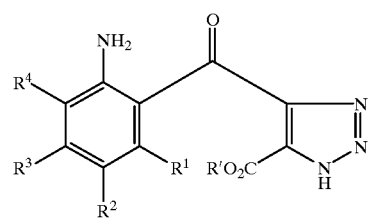

XIII wherein R' is lower-alkyl, with a base or 2-hydroxypyridine to prepare a corresponding compound of the formula I wherein C is a triazole ring.

The invention futer relates to the use of a compound of the Formula I for the preparation of a medicament for the treatment of neurological disorders.

The term lower-alkyl as used herein means linear or branched hydrocarbon chains having from one to about six carbon atoms and thus includes methyl, ethyl, propyl, isopropyl, n-butyl, sec-butyl, isobutyl, tert-butyl, 1-methylbutyl, 3-methylbutyl, n-pentyl, is 1-methylpentyl, 1-ethylbutyl, n-hexyl, and the like.

The term perfluorolower-alkyl as used herein means linear or branched hydrocarbon chains having one to about 4 carbon atoms wherein each hydrogen atom has been replaced by a fluorine atom and thus includes trifluoromethyl, pentafluoro-ethyl, heptafluoropropyl and the like.

The term halogen, halo, or halide as used herein means chlorine, bromine, iodine and fluorine.

The term lower-alkenyl as used herein means linear or branched unsaturated hydrocarbon radicals having two to about seven carbon atoms and thus includes ethenyl, 1-propenyl, 2-propenyl, isopropenyl, 1-methyl-2-propenyl, 2-butenyl, 3-butenyl, 1-methyl-3-butenyl, 3-methyl-3-butenyl, isobutenyl, 4-pentenyl, 3-hexenyl, 5-hexenyl, 6-heptenyl and the like.

The term lower-alkynyl as used herein means linear or branched unsaturated radicals having two to about seven carbon atoms and thus includes ethynyl, 1-propynyl, 2-propynyl, 1-methyl-2-propynyl, 2-butynyl, 3-butynyl, 1-methyl-3-butynyl, 4-pentynyl, 5-hexynyl, 6-heptynyl and the like.

The term cycloalkyl as used herein means $C_3$ to $C_7$ saturated monocyclic hydrocarbon residues and thus includes cyclopropyl, cyclobutyl, cyclopentyl, cyclohexyl and cycloheptyl.

The term lower-alkoxy as used herein means linear or branched alkyloxy substituents having one to about six carbon atoms and thus includes methoxy, ethoxy, propoxy, isopropoxy, butoxy, sec-butoxy, isobutoxy, tert-butoxy, 1-methylbutoxy, 3-methylbutoxy, pentyloxy, 1-methylpentyloxy, 1-ethylbutoxy, hexyloxy and the like.

Throughout the specification the compounds of the invention will be named as azolobenzazepine derivatives and will be numbered as shown in the ring system illustrated hereinbelow.

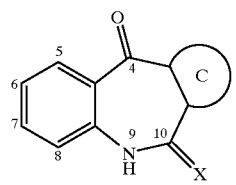

It will be appreciated that in the compounds of the formula I the 5-membered aromatic heterocycles represented by ring C can exist in a number of tautomeric forms. For example. (a) when C is a pyrazole ring the compounds of the Formula I can be represented by the formulas Ia and Ib and Ia

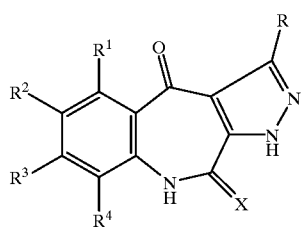

Ib

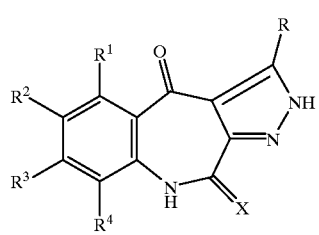

named as pyrazolo[3,4-c][1]benzazepine-4,10(1H,9H) or (2H,9H)-diones, respectively, when X is O, or 10-thioxo-pyrazolo[3,4-c][1]benzazepine-4(1H,9H) or (2H,9H)-ones, respectively, when X is S; and (b) when C is a triazole ring the compounds of the Formula I can be represented by the formulas Ic, Id and Ie and named as 1,2,3-triazolo[4,5-c]-[1]benzazepine-4,10(1H,9H), (2H,9H) or (3H,9H)-diones, when X is O, or 10-thioxo-1,2,3-triazolo[4,5-c][1]benzazepine-4(1H,9H), (2H,9H) or (3H,9H)-ones wherein X is S. While the compounds of the formula I, wherein C is a pyrazole or triazole ring, will be represented by the formulas Ia and Ic, respectively, throughout the specification, it will be appreciated that the invention is intended to extend to each of the various tautomeric forms (i.e. Formulas Ia–Ie) or to mixtures thereof.

Ic

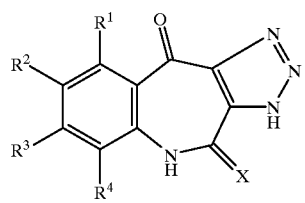

Id

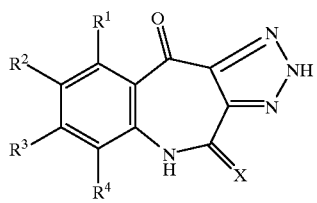

Ie

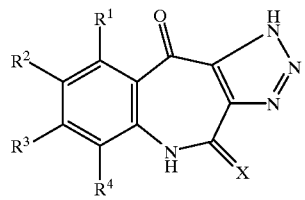

The synthesis of the compounds of the Formula I wherein C is a pyrazole ring and X is O, may be outlined as shown in Scheme A:

Scheme A

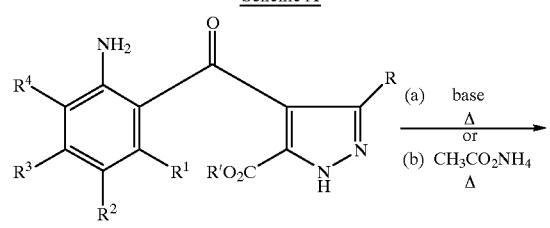

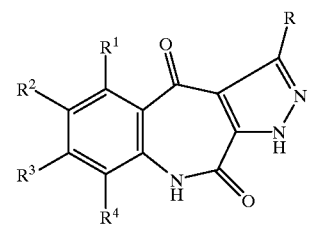

A suitably substituted 4-(2-aminobenzoyl)-1H-pyrazole-5-carboxylate of the formula II, wherein R' is lower-alkyl, preferably ethyl, in an appropriate organic solvent, such as toluene, is treated with about one mole of a base or 2-hydroxypyridine, preferably 2-hydroxypyridine, at a temperature in the range of about room temperature up to the boiling point of the solvent used, preferably at the boiling point of the solvent used, and then the organic solvent is removed and the remaining residue is heated at a temperature in the range of about 160° C. to about 170° C. to afford the compounds of the formula I wherein C is a pyrazole ring and X is O. Alternatively, the compounds of the formula I wherein C is a pyrazole ring and X is O can be prepared by treating a suitably substituted compound of the formula II, wherein R' is lower-alkyl, preferably ethyl, in an appropriate organic solvent, preferably 1-methyl-2-pyrrolidinone, with at least one mole of an ammonium salt, preferably ammonium acetate, at a temperature in the range of about room temperature up to the boiling point of the solvent used, preferably at about 160° C.

Alternatively, various compounds of the formula I wherein X is O, C is a pyrazole ring and R is —C(O)NR$^6$R$^7$ can be prepared as shown in Scheme B.

Scheme B

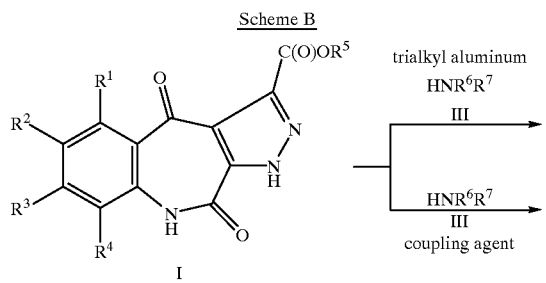

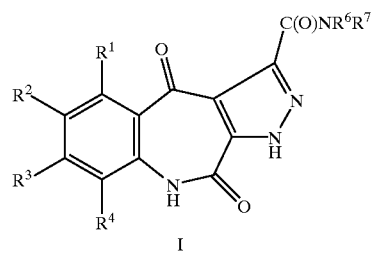

A compound of the formula I wherein X is O, C is a pyrazole ring, R is —C(O)OR$^5$ and R$^5$ lower-alkyl, preferably ethyl, in an appropriate organic solvent, such as toluene, is treated with a molar excess of a dialkylaluminum-NR$^6$R$^7$ reagent (prepared by treating a molar excess of a trialkylaluminum derivative, preferably trimethylaluminum, in an appropriate organic solvent, preferably toluene, with a molar excess of an amine of the formula III, HNR$^6$R$^7$) at a temperature in the range of about 0° C. up to about room temperature, to afford the corresponding compounds of the formula I wherein X is O, C is a pyrazole ring and R is —C(O)NR$^6$R$^7$. Alternatively, a compound of the formula I wherein X is O, C is ia pyrazole ring, R is —C(O)OR$^5$ and R$^5$ is hydrogen in an appropriate organic solvent, such as dimethylformamide, can be treated with a molar excess of a coupling agent, preferably 1,1'-carbonyldiimidazole, followed by a molar excess of an amine of the formula III, at a temperature in the range of about room temperature up to about 50° C., preferably at about 50° C., to afford the compounds of the formula I wherein X is O, C is a pyrazole ring and R is —C(O)NR$^6$R$^7$.

Alternatively, various compounds of the formula I wherein X is O, C is a pyrazole ring, R is —C(O)OR$^5$ and R$^5$ is other than hydrogen, can be prepared as shown in Schemes C and D.

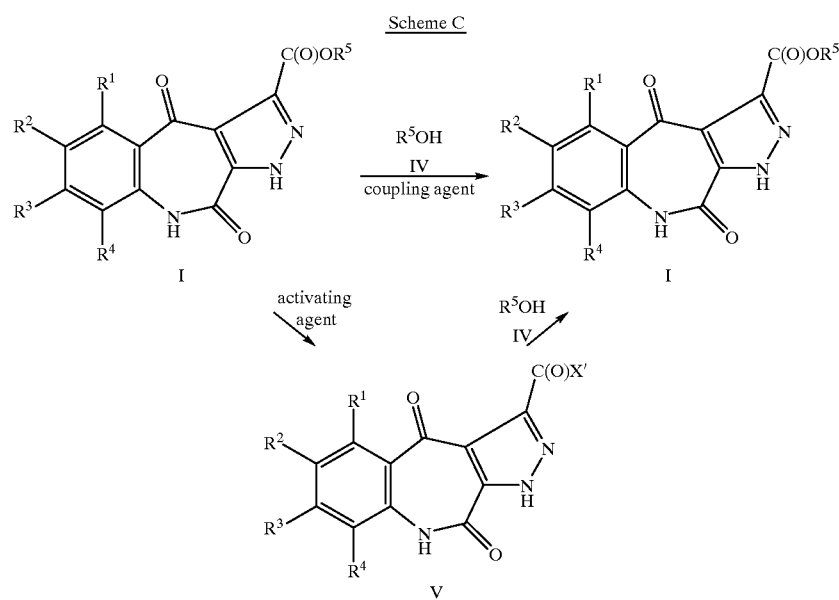

As shown in Scheme C, a compound of the formula I wherein X is O, C is a pyrazole ring, R is —C(O)OR and R$^5$ is hydrogen, in an appropriate organic solvent, such as dimethylformamide, is treated with a molar excess of an appropriate coupling agent, preferably 1,1'-carbonyldiimidazole, followed by a molar excess of an appropriate compound of the formula IV wherein $R^5$ is other than hydrogen, at a temperature in the range of about room temperature up to about 70° C., to afford the corresponding compounds of the formula I wherein X is O, C is a pyrazole ring, R is —C(O)OR$^5$ and $R^5$ is other than hydrogen. Alternatively, a compound of the formula I wherein X is O, C is a pyrazole ring, R is —C(O)OR$^5$ and $R^5$ is hydrogen, in an appropriate halogenated solvents such as dichloromethane containing a few drops of dimethylformamide, is treated with a molar excess of an activating agent, such as oxalyl chloride, at a temperature of about room temperature, to afford the compounds of the formula V wherein X' is halogen, preferably chlorine. The compound of the formula V can then be treated with an excess of a compound of the formula IV wherein $R^5$ is other than hydrogen, at a temperature in the range of about room temperature up to about 100° C. preferably at about 100° C. to afford the compounds of the formula I wherein X is O, C is a pyrazole ring, R is —C(O)OR$^5$ and $R^5$ is other than hydrogen.

In those instances wherein a compound of the formula I wherein X is O, C is a pyrazole ring and R is a formyl group is desired, it is preferred to proceed as illustrated in Scheme E. A suitably substituted compound of the formula I, wherein X is O, C is a pyrazole ring, R is —C(O)NR$^6$R$^7$ and $R^6$ is lower-alkyl and $R^7$ is lower-alkoxy, preferably $R^6$ is methyl and $R^7$ is methoxy, in an appropriate organic solvent, such as dimethylformamide, is treated with an excess of an alkylating agent of the formula VI, wherein X is a halogen, preferably chlorine, in the presence of a sodium halide, preferably sodium iodide, and an excess of an appropriate base, such as sodium carbonate, at a temperature in the range of about 0° C. up to about room temperature, to afford the compounds of the formula VII. The compound of the formula VII, in an appropriate organic solvent, such as tetrahydrofuran, can then be treated with an appropriate reducing agent, such as Scheme D

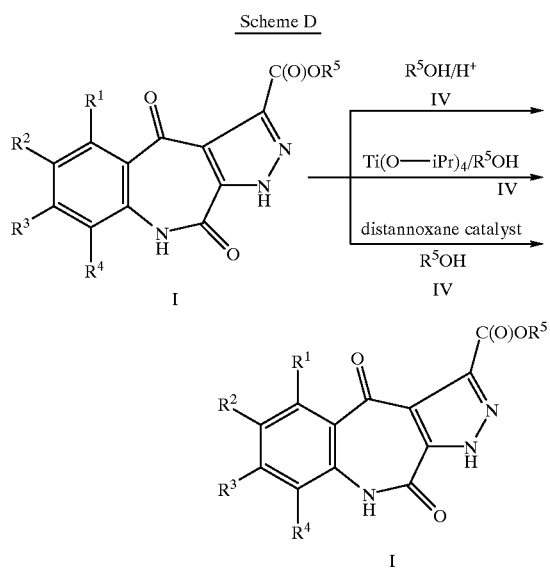

As shown in Scheme D, a suitably substituted compound of the formula I wherein X is O, C is a pyrazole ring, R is —C(O)OR$^5$ and $R^5$ is lower-alkyl, preferably ethyl, can be treated with (a) a molar excess of a compound of the formula IV, wherein $R^5$ is other than hydrogen, in the presence of an acid catalyst, such as hydrochloric acid, at a temperature of about room temperature up to the boiling point of the reaction mixture, preferably at the boiling point of the reaction mixture, (b) with a molar excess of a compound of the formula IV, wherein $R^5$ is other than hydrogen, in the presence of a molar excess of a titanium IV isopropoxide catalyst, at a temperature in the range of about room temperature up to the boiling point of the reaction mixture, preferably at the boiling point of the reaction mixture, or (c) with a molar excess of a compound of the formula IV, wherein $R^5$ is other than hydrogen, in the presence of at least one mole of a distannoxane catalyst, preferably 1-hydroxy-3-(isothiocyanato)tetrabutyl distannoxane, in an appropriate organic solvent, such as toluene, at a temperature in the range of about room temperature up to the boiling point of the reaction mixture, preferably at the boiling point of the reaction mixture, to afford the corresponding compounds of the formula I wherein X is O, C is a pyrazole ring, R is —C(O)OR$^5$ and $R^5$ is other than (a) hydrogen or (b) the $R^5$ group which was present in the starting material.

Scheme E

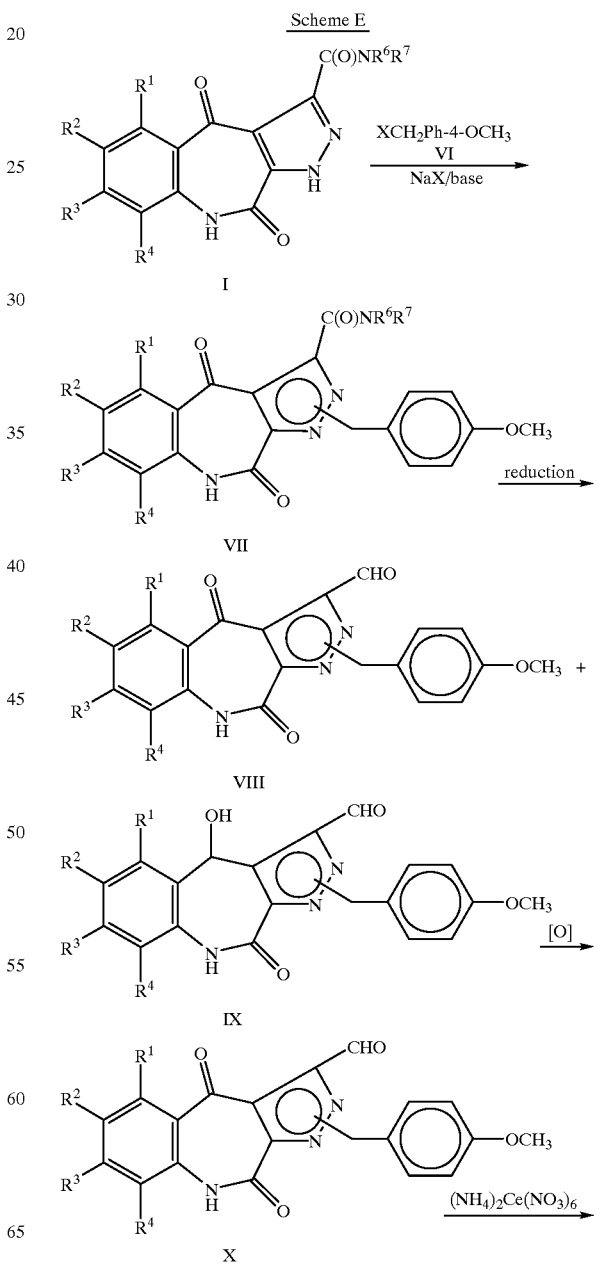

-continued

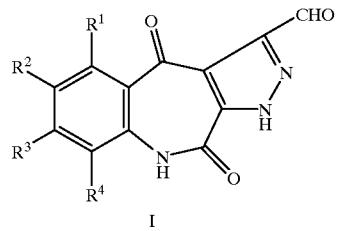

I diisobutylaluminum hydride (DIBAL™) at a temperature of about −78° C., to afford the compounds of the formulas VIII and IX. The compounds of the formula VIII and IX in an appropriate halogenated organic solvent, such as dichloromethane, can then be treated with excess of an appropriate oxidizing agent, preferably chromium (VI) oxide, in the presence of an excess of a base, preferably pyridine, at a temperature of about room temperature, to afford the compounds of the formula X. The compounds of the formula X, in an appropriate organic solvent/water mixture, such as acetonitrile/water, can then be treated with an excess of ceric ammonium nitrate, at a temperature of about room temperature, to afford the desired compounds of the formula I wherein X is O, C is a pyrazole ring and R is a formyl group.

In those instances wherein a compound of the formula I wherein X is O, C is a pyrazole ring and R is a lower-alkoxy carbonyl-lower-alkyl group is desired, it is preferred to proceed as illustrated in Scheme F:

Scheme F

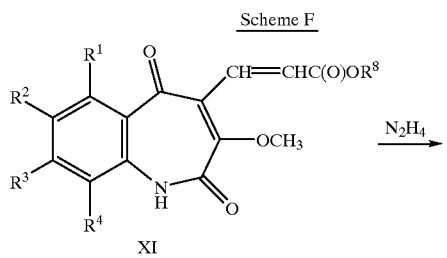

XI $N_2H_4$

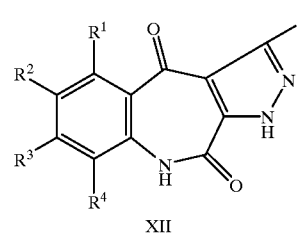

XII

A suitably substituted 2,5-dioxo-2,5-dihydro-1H-benz[b]azepine derivative of the formula XI, wherein $R^8$ is lower-alkyl, in an appropriate alcoholic solvent, such as methanol, is treated with an excess of hydrazine, at a temperature of about room temperature to afford the desired compounds of the formula XII (compound of Formula I wherein X is O, C is a pyrazole ring and R is a lower-alkoxycarbonyl-lower-alkyl group)

The synthesis of the compounds of the formula I, wherein C is a triazole ring and X is O, may be outlined as shown in Scheme G:

Scheme G

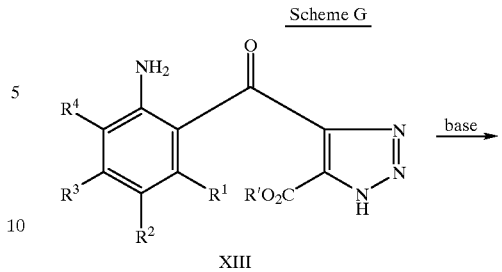

XIII base

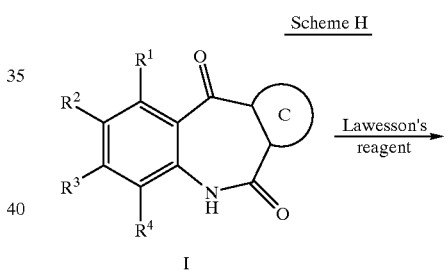

I

A suitably substituted 4-(2-aminobenzoyl)-1H-1,2,3-triazole-5-carboxylate of the formula XIII, wherein R' is lower-alkyl, preferably ethyl, in an appropriate organic solvent, such as tetrahydrofuran, is treated with a molar excess of a base, such as potassium t-butoxide or 2-hydroxypyridine, at a temperature in the range of about room temperature up to about 170° C., to afford the appropriate triazole derivatives of the formula I.

The compounds of the formula I wherein X is S can be prepared as described in Scheme H:

Scheme H

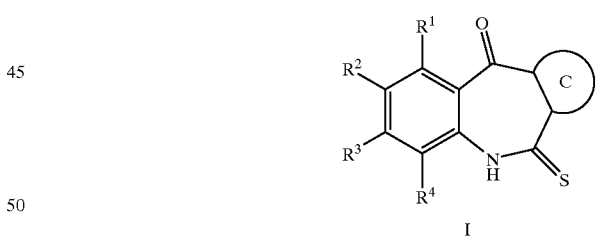

A suitably substituted compound of the formula I wherein X is O, in an appropriate organic solvent, such as toluene, is treated with Lawesson's reagent (2,4-bis(4-methoxyphenyl)-1,3-dithia-2,4-diphosphetane-2,4-disulfide), preferably 0.5 equivalents, at a temperature of about room temperature to afford the corresponding compounds of the formula I wherein X is S.

Simple chemical transformations which are conventional and well known to those skilled in the art of chemistry can be used for effecting changes in the functional groups of the compounds of the formula I to produce other compounds of the formula I. For example, (1) treating acids with ammonium acetate in the presence of an appropriate coupling agent, such as 1,1'-carbonyldiimidazole, to afford the corresponding amide (C(O)NH$_2$) derivatives, (2) the hydrolysis of esters to afford the corresponding carboxylic acid derivatives, (3) the treatment of carbamoyl (—C(O)NH$_2$) groups with a phosphorous oxyhalide, preferably phosphorous oxychloride, to afford the corresponding nitrile (—CN) derivatives, and (4) treating a carboxylic acid derivative with an activating agent such as phosphorous pentachloride or oxalyl chloride, to afford the corresponding acid halide and thereafter treating the acid halide with an amine of the formula III (HNR$^6$R$^7$) to afford the corresponding compounds of the formula I which contain a —C(O)NR$^6$R$^7$ group.

It will be appreciated that certain compounds of the Formula I can possess one or more asymmetric carbon atoms and are thus capable of existing in a number of stereoisomeric forms, i.e., enantiomeric, diastereomeric and racemic forms. In addition, certain compounds of the Formula I, i.e., those containing a double bond, can exist in, and be isolated in, separate stereoisomeric forms (E and Z) about the double bond. Additionally, some compounds of the Formula I may also exhibit polymorphism. Unless otherwise specified herein, the invention is intended to extend to any of the enantiomeric, diastereomeric, racemic, stereoisomeric (E/Z) or polymorphic forms, or to mixtures thereof The different stereoisomeric forms may be separated one from the other by the following methods: (a) the separate enantiomers may be synthesized from chiral starting materials or the racemates may be resolved by conventional procedures which are well known in the art of chemistry such as chiral chromatography, fractional crystallization of diastereomeric salts and the like; and (b) the diastereomers and E/Z stereoisomers can be separated by conventional procedures which are well known in the art of chemistry such as chromatography, fractional crystallization and the like.

The compounds of Formula I are useful both in the free base form, and in the form of acid-addition salts, and both forms are within the purview of the invention. The acid-addition salts are often a more convenient form for use and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal orzanism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts.

However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

Likewise, the compounds of the Formula I which contain acidic functions, e.g., carboxylic acids, are useful both in the free acid form and in the form of base-addition salts and both forms are within the purview of the invention. The base-addition salts are often a more convenient form for use and, in practice, use of the salt form inherently amounts to use of the free acid form. The bases which can be used to prepare the base-addition salts include preferably those which produce, when combined with the free acids pharmaceutically-acceptable salts, that is, salts whose cations are relatively innocuous to the animal organism in pharmaceutical doses of the salts, so that the beneficial properties inherent in the free acid are not vitiated by side effects ascribable to the cations. The base-addition salts can be prepared by the reaction of the free acid with a base, such as alkali metal or ammonium hydroxides or organic bases such as alkyl, dialkyl, or trialklamines, morpholine, piperidine, or triethanolamine. If desired, the free acids can be regenerated from the base-addition salts by treatment of the salts with an appropriate aqueous acid.

The suitably substituted 4-(2-aminobenzoyl)-1H-pyrazole-5-carboxylate derivatives of the formula II, which are required for the synthesis of the compound of the formula I, can be prepared as described in Scheme I. A suitably substituted 4-(2-nitrophenyl)-4-hydroxy-2-butynoate of the formula XIV.

Scheme I

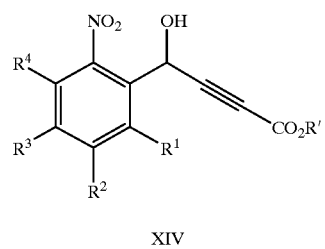
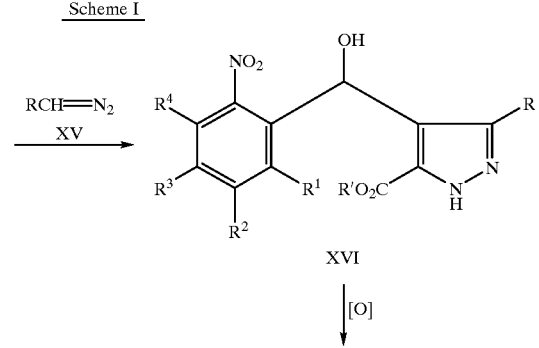

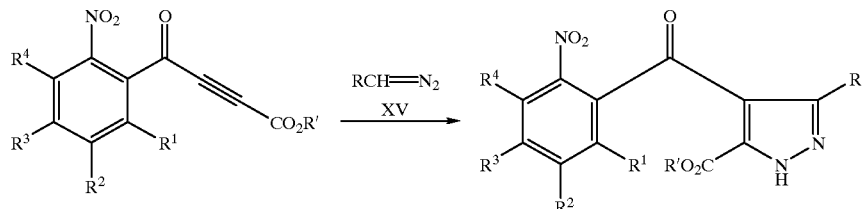

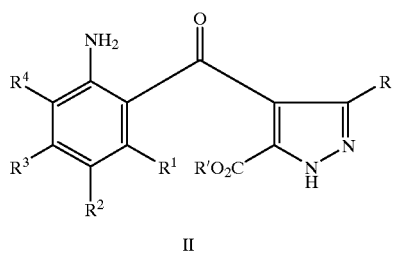

wherein R' is lower-alkyl, preferably ethyl, in an appropriate organic solvent, such as diethyl ether or tetrahydrofuran, is treated with at least one mole of a diazo compound of the formula XV, at a temperature in the range of about room temperature up to the boiling point of the reaction mixture, to afford the 4-(2-nitrophenylhydroxymethyl)-1H-pyrazole-5-carboxylate derivatives of the formula XVI. The compounds of the formula XVI can then be treated with a molar excess of an oxidizing agent, such as chromium (VI) oxide, in the presence of a molar excess of a base, preferably pyridine, in a halogenated solvent such as dichloromethane, at a temperature of about room temperature, to afford the 4-(2-nitrobenzoyl)-1H-pyrazole-5-carboxylate derivatives of the formula XVIII. Alternatively, the compounds of the formula XVIII can be prepared by treating a 4-(2-nitrophenyl)-4-oxo-2-butynoate of the formula XVII, in an appropriate organic solvent, such as tetrahydrofuran with a molar excess of a diazo compound of the formula XV, at a temperature of about room temperature. The compounds of the formula XVIII can then be treated with a molar excess of appropriate reducing agent, such as (1) sodium hydrosulfite or (2) nickel boride in the presence of an excess of an acid, preferably hydrochloric acid, in an appropriate solvent, preferably ethanol/water when sodium hydrosulfite is used or methanol when nickel boride is used, at a temperature in the range of about 0° C. up to the boiling point of the reaction mixture, to afford the compounds of the formula II.

The suitably substituted compounds of the formula XIII, which are required for the synthesis of the compounds of the formula I wherein C is a triazole ring, can be prepared as described in Scheme J:

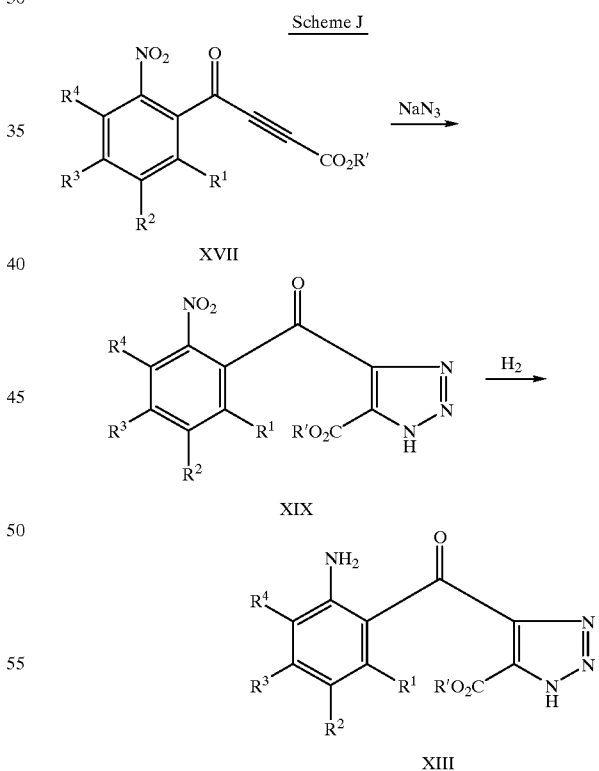

A suitably substituted 4-(2-nitrophenyl)-4-oxo-2-butynoate of the formula XVII, in an appropriate organic solvent, preferably dimethylformamide, can be treated with a molar excess of sodium azide, at a temperature in the range of about 0° C. up to about room temperature, to afford the 4-(2-nitrobenzoyl)-1H-1,2,3-triazole-5-carboxylates of the formula XIX. The compounds of the formula XIX, in an appropriate organic solvent or solvent mixture, preferably a mixture of ethanol/chloroform, can then be hydrogenated at about 50 psi in the presence of a catalyst, preferably $PtO_2$, to afford the compounds of the formula XIII.

The suitably substituted compounds of the formulas XIV and XVII, which are required for the synthesis of the compounds of the formulas II and XIII, can be prepared as shown in Scheme K:

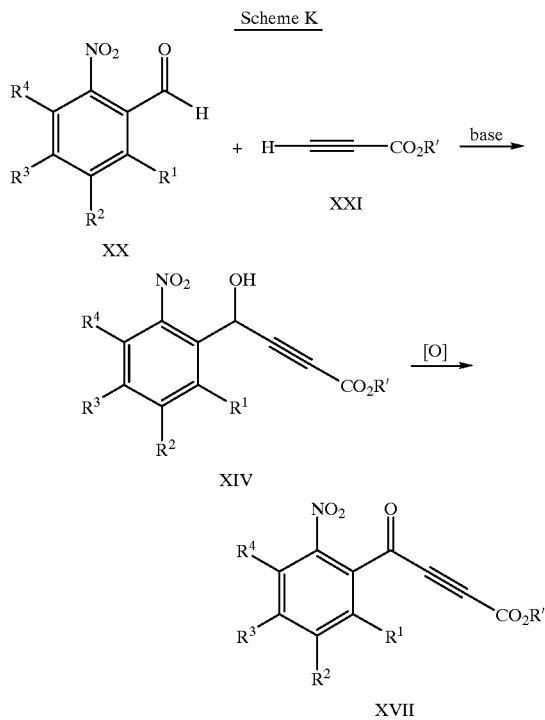

A suitably substituted aldehyde of the formula XX, in an appropriate organic solvent, such as tetrahydrofyran, is reacted with a molar excess of an alkyne of the formula XXI, wherein R' is lower-alkyl, preferably ethyl, in the presence of a molar excess of a base, preferably n-BuLi, at a temperature in the range of about −78° C. up to about room temperature, preferably at about −78° C., to afford the compounds of the formula XIV. The compounds of the formula XIV, in an appropriate halogenated solvent, such as dichloromethane, can then be treated with a molar excess of an oxidizing agent, such as $MnO_2$, at a temperature in the range of about 0° C. up to about room temperature, to afford the compounds of the formula XVII.

The compounds of the formula XI can be prepared by the procedures described in PCT WO 94/29275, published Dec. 22, 1994, the entire contents of which are incorporated herein by reference. The compounds of the formula III, IV, VI, XV, XX and XXI are either commercially available, or they can be prepared by procedures known in the art, or by the procedures described hereinbelow in the examples.

The following examples will further illustrate the invention without, however, limiting it thereto. Unless stated otherwise:

(i) temperatures are given in degrees Celsius (°C.): operations were carried out at room or ambient temperature, that is, at a temperature in the range of 18–25° C.;

(ii) evaporation of solvent was carried out using a rotate evaporator under reduced pressure (600–4000 pascals; 4.5–30 mm Hg) with a bath temperature of up to 60° C.;

(iii) flash chromatography was carried out on 40 μm silica gel flash chromatography packing obtained from J. T. Baker; thin layer chromatography (TLC) was carried out on Analtech 0.25 mm silica gel GHLF plates (Art 21521), obtainable from Analtech, Newark, Del., USA;

(iv) the course of the reactions and the identity and homogenity of the products were assessed by one or more of thin layer chromatography (TLC), high pressure liquid chromatography (HPLC), or gas-liquid chromatography (GLC), (v) melting points are uncorrected and (dec) indicates decomposition; the melting points given are those obtained for the materials prepared as described; polymorphism may result in isolation of materials with different melting points in some preparations;

(vi) the structures of the compounds of the invention were established by the mode of synthesis, and by one or more of micro analytical (elemental analysis) data, infrared, or nuclear magnetic resonance (NMR) spectroscopy, or mass spectrometry;

(vii) yields and reaction times are given for illustration only;

(viii) reduced pressures are given as absolute pressures in Pascals (pa); other pressures are given as gauge pressures in bars;

(ix) chemical symbols have their usual meanings; the following abbreviations have also been used: v (volume), w (weight); mp (melting point), L [liter(s)], mL (milliliters), mmol (millimoles), g [gram(s)], mg [milligram(s)], min. [minute(s)], hr. [hour(s)];

(x) solvent ratios are given in volume:volume (v/v) terms, unless indicated otherwise;

(xi) unless otherwise specified, reactions were run under an atmosphere of nitrogen ($N_2$); and (xii) the term continuous chromatography refers to the following process: A single-neck round bottom flask is charged with solvent (half to two-thirds full) and equipped with a pressure-equalizing addition funnel which is topped with a reflux condenser. A plug of glass wool is inserted into the addition funnel just above the stopcock and silica gel is added to the addition funnel until it is half to two-thirds full. The stopcock is opened, a solution of the compound is applied to the top of the silica gel and the apparatus is purged with nitrogen. The solvent in the flask is heated so that it refluxes into the condenser and drips onto the top of the silica gel, passing through the silica gel and back into the round bottom flask. The progress of the purification can be monitored by tlc of the solution in the flask. Fractions can be obtained or solvent changed simply by switching flasks.

EXAMPLE 1

(a) Ethyl 4-(4-chloro-2-nitrophenyl)-4-hydroxy-2-butynoate

To a cooled (−78° C.) solution of ethyl propiolate (8.96 mL, 88.4 mmol) in THF (100 mL) was added n-butyllithium (37.5 mL of 2.37M solution in hexane, 88.9 mmol) dropwise over 70 minutes so as to maintain the internal temperature below −70° C. Additional THF (5 mL) was used to rinse the addition funnel. A solution of 4-chloro-2-nitrobenzaldehyde (14.88 g, 80.2 mmol) in THF (30 mL) was transferred to the addition fiunel and added dropwise is over 47 minutes to maintain the reaction temperature below −70° C. Additional THF (5 mL) was used to rinse the addition funnel. The solution was stirred for 90 minutes at −70° C. and was then warmed to −60° C. glacial acetic acid (18.3 mL, 316 mmol) was quickly added. The solution was allowed to warm to 10° C. over 60 minutes and poured into diethyl ether (900 mL). The resulting solution was washed with saturated aqueous sodium carbonate (2×450 mL) and saturated aqueous sodium chloride (1×450 mL). The organic layer was dried over anhydrous sodium sulfate, filtered, and concentrated on a rotary evaporator. This product was purified by flash chromatography eluting with ethyl acetate:hexanes (90:10) to give the title compound as red oil (14.73 g, 64.8%).

The 4-chloro-2-nitrobenzaldehyde starting material can be prepared as follows: Borane dimethylsulfide (156 mL, 1.55 moles) was added to a stirred solution of 4-chloro-2-nitro-benzoic acid (313.0 g, 1.55 moles) and dry tetrahydrofuran (2 L) at room temperature under $N_2$ until about 30 mL had been added. The reaction mixture was then heated to gentle reflux. The rest of the borane dimethylsulfide was added dropwise (3 mL/min) with heating to maintain the temperature at gentle reflux. Heating at reflux was continued for 2.5 hours after addition was completed. Additional borane dimethylsulfide (20 mL, 0.2 mole) was added to the reaction mixture and heating was continued for 10 minutes. The reaction mixture was allowed to cool to room temperature and the reaction mixture was concentrated under water aspirator vacuum. The residue was dried under vacuum, then was dissolved in methylene chloride (1.7 L) and the solution was added (15 minutes) to a stirred mixture of pyridinium chlorochromate (375 g, 1.74 moles) and methylene chloride (3 L) under $N_2$. Stirring was continued at room temperature for 0.5 hours, then the reaction mixture was heated at reflux for 1.5 hours. Additional pyridinium chlorochromate (110 g, 0.51 mole) was added and heating at reflux was continued for 1.5 hours. The reaction mixture was allowed to cool to room temperature and diethyl ether (3 L) was added with stirring. The mixture with filtered through CELITE™ and the pad was flushed with diethyl ether (2×500 mL). The filtrate and wash liquors were combined and filtered twice through silica gel (1200 mL) and (1200 mL). The filtrate was concentrated under water aspirator vacuum. The residue was dried under vacuum to give 4-chloro-2-nitro-benzaldehyde as a yellow powder (247.32 g, 86%).

(b) Diethyl 4-[(4-chloro-2-nitrophenyl) hydroxymethyl]-1H-pyrazole-3,5-dicarboxylate A solution of ethyl 4-(4-chloro-2-nitrophenyl)-4-hydroxy-2-butynoate (5.00 g, 17.7 mmol) and ethyl diazoacetate (2.75 g, 26.5 mmol) in diethyl ether (43.3 mL) was refluxed for 5 days. After cooling to room temperature the reaction mixture was chromatographed eluting with ethyl acetate:hexanes (20:80, 30:70, 40:60, and 50:50). All of the fractions containing the desired compound were combined, concentrated on the rotary evaporator, and the product was recrystallized twice from toluene (total volume 225 mL) to give the title compound as a white solid (4.15 g, 59%, mp 60° C.).

Alternatively, the title compound can be prepared as follows:

A mixture of ethyl 4-(4-chloro-2-nitrophenyl)-4-hydroxy-2-butynoate (253 g, 0.89 mole), ethyl diazoacetate (102 g, 0.89 mole) and dry tetrahydrofuran (1.4 L) was heated at reflux with stirring under $N_2$ for 3 days. Additional ethyl diazoacetate (40.0 g, 0.35 mole) was added and heating at reflux was continued for 18 hours. The solvent was removed under water aspirator vacuum. The residue (409 g) was dissolved in toluene (800 mL) and hexane (800 mL) was slowly added to the solution and the resultant mixture was stirred for 1 hour. The mixture was filtered. The filter cake was washed with hexane (1 L) and dried to give a tan-yellow powder (216.4 g) This tan-yellow powder was dissolved in hot toluene (1.0 L) and hexane (1 L) was added dropwise to the warm stirred solution. The stirring mixture was allowed to cool to room temperature while stirring overnight. The mixture was filtered. The filter cake was washed with hexane (2×500 mL) and dried at 50° C. under vacuum to give the title compound as an off-white powder (202.55 g, 57%). The above filtrate was concentrated under water aspirator vacuum. The residue (123 g) was placed on a silica gel (5 L) column and flash eluted with methylene chloride:methanol, 99.5:0.5 to 98:2, to give additional title compound as an off-white powder (9.85 g, 2.78%).

(c) Diethyl 4-(4-chloro-2-nitrobenzoyl)-1H-pyrazole-3,5-dicarboxylate

Chromium (VI) oxide (17.48 g, 174.8 mmol) was added over 37 minutes to a solution of pyridine (27.6 mL, 349.5 mmol) in dichloromethane (400 mL). Diethyl 4-[(4-chloro-2-nitro-phenyl)hydroxymethyl]-1H-pyrazole-3,5-dicarboxylate (11.56 g, 29.1 mmol) was added as a solid over 9 minutes. The reaction mixture was allowed to stir at room temperature 44 is hours. The solution was filtered and the organic layer was washed with aqueous hydrochloric acid (500 mL, 3N). The aqueous layer was extracted with ethyl acetate (3×250 mL) and dichloromethane (3×250 mL). The resulting organic extracts were combined and concentrated on the rotary evaporator to give a crude solid (10.92 g). The product was purified by chromatography eluting with dichloromethane:2-propanol (98:2, 96:4, and 94:6). The desired product was obtained from the mixed fractions by recrystallization from toluene (250 mL). Clean fractions from chromatography were combined with recrystallized product to give the title compound as a white solid (9.85 g, 86%, mp 168° C.).

Alternatively, the title compound can be prepared as follows:

Pyridine (481.6 g, 6.08 moles) was added dropwise over 35 minutes to a mechanically stirred suspension of chromium (VI) oxide (304.56 g, 3.05 moles) (WARNING: adding pyridine to chromium (VI) oxide is an extremely dangerous procedure and, therefore, chromium (VI) oxide should preferably be added to pyridine) and methylene chloride (6 L) under $N_2$. The reaction as stirred for 40 minutes after pyridine addition was completed and then a solution of diethyl 4-[(4-chloro-2-nitro phenyl) hydroxymethyl]-1H-pyrazole-3,5-dicarboxylate (202.5 g, 0.507 mole) in methylene chloride (1.3 L) was added dropwise over 0.5 hours at room temperature. Stirring at room temperature was continued overnight. CELITE™ (205 g) and additional Collins reagent [chromium (VI) oxide (50 g, 0.5 mole) and pyridine (120.3 g, 1.52 moles, methylene chloride (1 L)] were added and the reaction mixture was stirred for 4 days. The reaction mixture was filtered. The filter cake was washed with methylene chloride (3 L) and filtered. The filtrate and wash liquors were combined and concentrated under water aspirator vacuum. The residue was dissolved in ethyl acetate(2 L) and this solution was filtered through a short column of silica gel (3 L). The filtrate was concentrated under water aspirator vacuum. The solid residue was dissolved in warm toluene (800 mL) and then hexane (800 mL) was added with stirring. The mixture was allowed to cool to room temperature and was then filtered. The filter cake was washed with hexane (2×500 mL), and dried under vacuum at 50° C. to give the title compound as a white powder (186.08 g, 93%).

(d) Diethyl 4-(4-chloro-2-aminobenzoyl)-1H-pyrazole-3,5-dicarboxylate

To absolute ethanol (265 mL) was added diethyl 4-(4-chloro-2-nitrobenzoyl)-1H-pyrazole-3,5-dicarboxylate (8.7 g, 22.25 mole). The mixture was stirred 20 minutes and then was slowly heated to reflux. A solution of sodium hydrosulfite (15.29 g, 87.86 mmol) in water (85.5 mL) was added in portions over 4 hours. The solution was refluxed 4 days. The mixture was allowed to cool and the solid was filtered off. The organic layer was concentrated on a rotary evaporator to give a yellow solid (18.23 g). This crude product was purified by flash chromatography eluting with ethyl acetate-:hexanes (15:85, 25:75, 30:70) to give a yellow solid (3 g). The mixed fractions containing the inorganic material and product were concentrated on a rotary evaporator and the product was continuously chromatographed eluting with chloroform:2-propanol (98:2). The product was concentrated on a rotary evaporator and combined with clean fractions from the first column to give the title compound as a yellow solid (combined weight 5.2 g, 64%, mp 201° C.).

Alternatively, the title compound can be prepared as follows: A mixture of nickel acetate (444 g, 1.78 moles) and water (6.6 L) was cooled to 8° C. with stirring under nitrogen: then a solution of sodium borohydride (271 g, 7.16 moles) in water (3.55 L) was added dropwise over 1.5 hours maintaining the reaction temperature between 8° C. and 12° C. The reaction mixture was then stirred for 1.5 hours at 8–12° C. The reaction mixture was filtered through a coarse scintered glass filter funnel, keeping, the black filter cake wet (Caution: this black powder may be pyrophoric if allowed to dry). The filter cake was washed first with water (6×2 L), then with ethanol (2×2 L) and finally with methanol (1 L). The methanol wet filter cake ($Ni_2B$, pyrophoric) was transferred to a 22 L flask with methanol (8 L). A solution of diethyl 4-(4-chloro-2-nitrobenzoyl)-1H-pyrazole-3,5-dicarboxylate (111.0 g, 0.28 mole) in hydrochloric acid (2.52 L) was added. The reaction mixture was heated to 64° C. and was kept at 64° C. for 6 hours; then was allowed to cool to room temperature and was filtered through CELITE™. The CELITE™ layer was washed with methanol (2×2 L). The filtrate and wash liquors were combined and the methanol was distilled off under water aspirator vacuum. Water (1 L) was added to the reaction and the mixture was filtered. The filter cake was washed with water (2×500 mL) and dried under vacuum at 40° C. to give the title compound as a yellowish solid (98.81 g, 96%).

(e) 7-Chloro-3-(ethoxycarbonyl)pyrazolo[3,4-c][1]benzazepine-4,10-(1H,9H)dione

To a solution of 2-hydroxypyridine (1.30 g, 13.69 mmol) in toluene (400 mL) was added diethyl 4-(4-chloro-2-aminobenzoyl)-1H-pyrazole-3,5-dicarboxylate (5 g, 13.69 mmol). The mixture was refluxed for 2 days and then the solvent was distilled off and the residual solid was heated at 171–172° C. for 4 days. The solid was allowed to cool and was continuously chromatographed eluting for 2 hours with dichloromethane to remove starting material. The remaining material on the column was eluted with chloroform:2-propanol (97:3) for 4 days. After each day the solvent in the receiving flask was replaced with fresh solvent. Filtering the solvent from the first two receiving flasks gave the title compound as a white solid (1.65 g, 38%, mp 290° C.). Alternatively, the title compound can preferably be removed from the column by elution with ethanol/chloroform (7:93).

Alternatively, the title compound can be prepared as follows: A mixture of diethyl 4-(4-chloro-2-aminobenzoyl)-1H-pyrazole-3,5-dicarboxylate (133.64 g, 0.365 mole), ammonium acetate (2.82 g, 0.0365 mole), and 1-methyl-2-pyrrolidinone (267 mL) was heated with stirring at 160° C. under $N_2$ for 14 hours. After cooling to room temperature, the reaction mixture was poured into water (4 L) with stirring. Stirring was continued for 0.5 hours, then the mixture was filtered. The filter cake was suspended in water (3 L), stirred for 0.5 hours and filtered. The filter cake was washed with water (3×600 mL) and dried under vacuum to give an off-white powder (110.3 g). This product was washed with methylene chloride (1 L) and dried under vacuum to give an off-white powder (105.23 g). This sample was recrystallized from glacial acetic acid and filtered. The filter cake was washed with water and dried under vacuum at 50° C. to give the title compound as a white powder (67.7 g, 59%).

EXAMPLE 2

7-Chloro-3-[(2-methoxyethyl)carbamoyl]pyrazolo[3,4-c][1]-benzazepine-4,10(1H,9H)-dione To a solution of trimethylaluminum in toluene (5.34 mL, 10.7 mmol) was added 2-methoxyethylamine (0.93 mL, 10.7 mmol) and the solution was stirred for 0.5 hours. A portion (0.63 mL) of this solution was added to a solution of 7-chloro-3-(ethoxycarbonyl)pyrazolo-[3,4-c][1]benzazepine-4,10(1H,9H)-dione (171 mg, 0.534 mmol) in toluene (1.3 mL). The resulting solution was stirred 4.5 hours at room temperature and then was quenched by the addition of aqueous hydrochloric acid (1.6 mL, 1N) and water (50 mL). The layers were separated and the aqueous layer was extracted with ethyl acetate (5×30 mL) and methylene chloride (5×30 mL). The combined organics were concentrated on a rotary evaporator to yield a crude solid (70 mg). The aqueous layer was diluted with water (300 mL) and continuously extracted with chloroform (250 mL) for 64 hours. The chloroform was concentrated on a rotary evaporator to yield a solid (60 mg). Both solids were combined and purified by flash chromatography eluting with methylene chloride:2-propanol (95:5, 90:10, 80:20) to give the title compound, (41% yield, m.p. 287–291° C.). Alternatively, the title compound can preferably be removed from the column by elution with ethanol:chloroform (7:93).

EXAMPLE 3

7-Chloro-3-(dipropylcarbamoyl)pyrazolo[3,4-c][1]benzazepine-4,10(1H,9H)-dione

To a solution of trimethylaluminum in toluene (4.68 mL 9.38 mmol) was added dipropylamine (1.29 mL, 9.38 mmol) and the solution was stirred for 45 hours. A portion (1.9 30 mL) of this solution was added to a solution of 7-chloro-3-(ethoxycarbonyl)pyrazolo[3,4-c][1]benzazepine-4,10(1H,9H)-dione (500 mg, 1.56 mmol) in toluene (2 mL). Additional toluene (7 mL) was added. The solution was stirred for 70 minutes at room temperature and then quenched with 1N hydrochloric acid (9.3 mL). The layers were separated and the aqueous layer was extracted with ethyl acetate (3×50 mL). The combined organics were washed with 1N hydrochloric acid and water (25 mL) and concentrated by rotary evaporation. The crude residue was purified by chromatography eluting with hexanes:ethyl acetate (95:5–50:50) to give the title compound (31% yield, m.p. 270° C.).

EXAMPLE 4

7-Chloro-3-(N-benzylcarbamoyl)pyrazolo[3,4-c][1]benzazepine-4,10(1H,9H)-dione

Benzylamine (1.34 mL, 12.5 mmol) was added to a solution of trimethylaluminum in toluene (6.25 mL, 12.5 mmol) and the solution was stirred for 30 minutes. A portion (759 µL) of the resulting solution was added to a solution of 7-chloro-3-(ethoxycarbonyl)pyrazolo[3,4-c][1] benzazepine-4,10(1H,9H)-dione (200 mg, 0.625 mmol) in toluene (1.56 mL). The resulting solution was stirred 48 hours at room temperature and then quenched with aqueous hydrochloric acid (1.88 mL, 1N) and water (30 mL). The aqueous layer phase was extracted with dichloromethane (5×25 mL). The organic layers were combined and the insoluble material was filtered and dried to give the title compound (203 mg, 85% yield, m.p. 335–336° C.).

EXAMPLE 5

7-Chloro-3-(morpholinocarbonyl)pyrazolo[3,4-c][1]-benzazepine-4,10(1H,9H)-dione

Morpholine (268 µL, 3.06 mmol) was added to a solution of trimethylaluminum in toluene (1.56 mL, 3.13 mmol) and the solution was stirred for 20 minutes. A portion (365 µL) of the resulting solution was added to a solution of 7-chloro-3-(ethoxycarbonyl)pyrazolo[3,4-c][1]benzazepine-4,10(1H,9H)-dione (100 mg, 0.313 mmol) in toluene (0.760 mL). The resulting solution was stirred for 4 hours at room temperature and then quenched with aqueous hydrochloric acid (1.88 mL, 1N) and water (50 mL). The aqueous layer was extracted with chloroforrn (7×50 mL) and ethyl acetate (3×50 mL). The combined organic layers were concentrated on a rotary evaporator. The crude product was purified by flash chromatography eluting with chloroform:2-propanol (99:1–80:20) to give the title compound (89.9 mg, 80% yield, m.p. 347° C.).

EXAMPLE 6

7-Chloro-3-[N,N-bis-(2-ethoxyethyl)carbamoyl] pyrazolo[3,4-c][1]benzazepine-4,10(1H,9H)-dione Bis-(2-ethoxyethyl)amine (560 µL, 3.13 mmol) was added to a solution of trimethylaluminum in toluene (1.56 mL, 3.13 mmol) and the solution was stirred for 20 minutes. A portion (424 µL) of the resulting solution was added to a solution of 7-chloro-3-(ethoxycarbonyl)pyrazolo[3,4-c][1] benzazepine-4,10(1H,9H)-dione (100 mg, 0.313 mmol) in toluene (780 µL). The resulting solution was stirred for 4.5 hours at room temperature and then quenched with aqueous hydrochloric acid (1.5 mL, 1N) and water (20 mL). The aqueous layer was extracted with ethyl acetate (3×50 mL) and the organic layers were concentrated on a rotary evaporator. The crude product was purified by flash chromatography eluting with chloroform:2-propanol (99:1–80:20) to give the title compound (60.8 mg, 45% yield, m.p. 202° C.).

EXAMPLE 7

7-Chloro-3-[N,N-bis-(2-methoxyethyl)carbamoyl] pyrazolo[3,4-c][1]benzazepine-4,10(1H,9H)-dione Bis-(2-methoxyethyl)amine (560 µL, 3.13 mmol) was added to a solution of trimethylaluminum in toluene (1.56 mL, 3.13 mmol) and the solution was stirred for 20 minutes. A portion (403 µL) of the resulting solution was added to a solution of 7-chloro-3-(ethoxycarbonyl)pyrazolo[3,4-c][1] benzazepine-4,10(1H,9H)-dione (100 mg, 0.313 mmol) in toluene (780 µL). The resulting solution was stirred for 24 hours at room temperature and then quenched with an aqueous hydrochloric acid solution (1.8 mL, 1N) and water (15 mL). The aqueous layer was extracted with chloroform (7×25 mL). The organic layers were combined and concentrated on a rotary evaporator. The crude product was purified by flash chromatography eluting with chloroform:2-propanol (99:1–95:5) to give the title compound (421 mg, 67% yield, m.p. 207–209° C.).

EXAMPLE 8

7-Chloro-3-[(N-methoxy-N-methylamino)carbonyl)] pyrazolo[3,4-c][1]benzazepine-4,10(1H,9H)-dione To N,O-dimethylhydroxylamine hydrochloride (550 mg, 5.6 mmol) was added trimethylaluminum in toluene (2.8 mL, 5.6 mmol) and the solution was stirred for 15 minutes at 0° C. A portion (1.5 mL) of the resulting solution was added to a solution of 7-chloro-3-(ethoxycarbonyl)pyrazolo [3,4-c][1]benzazepine-4,10(1H,9H)-dione (300 mg, 0.938 mmol) in toluene (5 mL) at 0° C. The resulting solution was allowed to warm to room temperature and was stirred for 4 hours. The solution was quenched with aqueous hydrochloric acid (8.4 mL, 1N) and water (50 mL). The aqueous layer was extracted with dichloromethane (8×30 mL) and the organic layers were concentrated by rotary evaporation to give a solid (160 mg). The aqueous layer phase was then continuously chromatographed with dichloromethane for 19 hours. The organic layer was concentrated by rotary evaporation to give a solid (190 mg). The two solids were combined and purified by flash chromatography eluting with dichloromethane:2-propanol (100% dichloromethane to 90:10). The fractions collected were combined and concentrated by rotary evaporation to give the title compound (220 mg, 70% yield, m.p. 287° C.).

EXAMPLE 9

7-Chloro-3-(carboxy)pyrazolo[3,4-c][1]benzazepine-4,10-(1H,9H)-dione

A solution of 7-chloro-3-(ethoxycarbonyl)pyrazolo[3,4-c] [1]benzazepine-4,10(1H,9H)-dione (6 g, 18.75 mmol) in aqueous sodium hydroxide (206 mL, 0.2N) was refluxed for 135 minutes. The mixture was cooled to room temperature and glacial acetic acid (30 mL) was added. The insoluble material was filtered and dried to give the title compound as a yellow solid (5.1 g, 94%, m.p. >400° C. dec.).

EXAMPLE 10

7-Chloro-3-[[(tert-butylamino)oxy]carbonyl] pyrazolo[3,4-c][1]benzazepine-4,10(1H,9H)-dione A solution of 7-chloro-3-(carboxy)pyrazolo[3,4-cl[1]-benzazepine-4,10(1H,9H)-dione (400 mg, 1.37 mmol) (compound of Example 9) and 1,1'-carbonyldiimidazole (334 mg, 2.06 mmol) in N,N-dimethylformamide (16 mL) was stirred for 1 hour. In one portion, N-tert-butylhydroxylamine hydrochloride (516 mg, 4.11 mmol) was added and the solution was stirred for 17 hours at room temperature. To the resulting solution was added water (20 mL). The insoluble material was filtered and washed with hot methanol (3×20 mL) to give the title compound (300 mg, 61% yield, m.p. 258° C.).

EXAMPLE 11

7-Chloro-3-[[(cyclohexylamino)oxy]carbonyl] pyrazolo[3,4-c][1]-benzazepine-4,10( 1H,9H)-dione A solution of 7-chloro-3-(carboxy)pyrazolo[3,4-c][1] benzazepine-4,10(1H,9H)-dione (300 mg, 1.03 mmol) (compound of Example 9) and 1,1'-carbonyldiimidazole (251 mg, 1.55 mmol) in N,N-dimethylformamide (12 mL) was stirred for 1 hour. In one portion N-cyclohexylhydroxylamine hydrochloride (469 mg, 3.09 mmol) was added and the solution was stirred for 2 hours at room temperature. To the resulting solution was added water (15 mL). The insoluble material was filtered and dried to give the title compound (286 mg, 72% yield, m.p. 220° C.).

EXAMPLE 12

7-Chloro-3-[[(isopropylamino)oxy]carbonyl]pyrazolo[3,4-c]-[1]benzazepine-4,10(1H,9H)-dione A solution of 7-chloro-3-(carboxy)pyrazolo[3,4-][1]benzazepine-4,10(1H,9H)-dione (300 mg, 1.03 mmol) (compound of Example 9) and 1,1'-carbonyldiimidazole (251 mg, 1.55 mmol) in N,N-dimethylformamide (12 mL) was stirred for 1 hour. In one portion N-isopropylhydroxylamine hydrochloride (345 mg, 3.09 mmol) was added and the solution was stirred for 55 minutes at room temperature. To the resulting solution was added water (40 mL) giving a precipitate which was separated by filtration. This crude product was purified by flash chromatography eluting with chloroform:2-propanol (98:2–96.5:3.5) to give the title compound (167 mg, 47% yield, m.p. 224° C.).

EXAMPLE 13

7-Chloro-3-[[(benzylamino)oxy]carbonyl]pyrazolo[3,4-c]-[1]benzazepine-4,10(1H,9H)-dione A solution of 7-chloro-3-(carboxy)pyrazolo[3,4-c][1]benzazepine-4,10(1H,9H)-dione (100 mg, 0.344 mmol) (compound of Example 9) and 1,1'-carbonyldiimidazole (83.5 mg, 0.515 mmol) in N,N-dimethylformamide (1.4 mL) was stirred for 1 hour. In a separate flask was placed N-benzylhydroxylamine hydrochloride (82.2 mg, 0.515 mmol), triethylamine (71.7 µL, 0.515 mmol), and N,N-dimethylformamide (2 mL). This solution was stirred for 20 minutes. The hydroxylamine solution was added to the acylimidazole solution and the resulting solution was stirred for 1 hour at 70° C. The solution was cooled to room temperature and water (10 mL) was added. The insoluble material was filtered and dried to give the title compound (110 mg, 81% yield, m.p. 169–179° C. dec.).

EXAMPLE 14

7-Chloro-3-(aminocarbonyl)pyrazolo[3,4-c][1]benzazepine-4,10(1H,9H)-dione

A solution of 7-chloro-3-(carboxy)pyrazolo[3,4c][1]-benzazepine-4,10-(1H,9H)-dione (1 g, 3.44 mmol) (compound of Example 9) and 1,1'-carbonyldiimidazole (0.64 mg, 3.95 mmol) in N,N-dimethylformamide (25 mL) was stirred for 64.5 hours. In one portion, ammonium acetate (0.796 mg, 10.33 mmol) was added, followed by additional N,N-dimethylformamide (15 mL). The solution was stirred for 3.75 hours at room temperature and concentrated in vacuo for 45 minutes. The residue was washed with water (3×20 mL). The insoluble material was filtered and dried to give the title compound (967 mg, 97% yield, m.p. 224–225° C.).

EXAMPLE 15

7-Chloro-3-(phenyloxycarbonyl)pyrazolo3,4-c][1]benzazepine-4,10(1H,9H)-dione

A solution of 7-chloro-3-(carboxy)pyrazolo[3,4-c][1]benzazepine-4,10(1H,9H)-dione (500 mg, 1.72 mmol) (compound of Example 9) and 1,1'-carbonyldiimidazole (418 mg, 2.58 mmol) in N,N-dimethylformamide (7 mL) was stirred for 16.75 hours. In one portion, phenol (486 mg, 5.16 mmol) was added and the solution was stirred for 24 hours at 70° C. To the resulting solution was added water (30 mL), giving a precipitate which was separated by filtration. This crude product was purified by chromatography eluting with chloroform:2-propanol (98:2–90:10) to give the title compound (330 mg, 53% yield, m.p. 265° C.).

EXAMPLE 16

7-Chloro-3-(benzyloxycarbonyl)pyrazolo[3,4-c[1benzazepine-4,10(1H,9H)-dione

A solution of 7-chloro-3-(carboxy)pyrazolo[3,4-c][1]benzazepine-4,10(1H,9H)-dione (500 mg, 1.72 mmol) (compound of Example 9) and 1,1'-carbonyldiimidazole (418 mg, 2.58 mmol) in N,N-dimethylformamide (7 mL) was stirred 13 minutes. In one portion benzyl alcohol (534 µL, 5.16 mmol) was added. The solution was stirred for 17.5 hours at room temperature and 2.75 minutes at 55° C. The solution was allowed to cool to room temperature and water (10 mL) was added. The insoluble material was filtered and dried to give the title compound (360 mg, 55% yield, m.p. 254° C.).

EXAMPLE 17

7-Chloro-3-(2-propenyloxycarbonyl)pyrazolo[3,4-c][1]benzazepine-4,10(1H,9H)-dione To a solution of 7-chloro-3-(carboxy)pyrazolo[3,4-c][1]benzazepine-4,10(1H,9H)-dione (500 mg, 1.7 mmol) (compound of Example 9) in dichloromethane (15 mL) was added N,N-dimethylformamide (2 drops) and then in one portion oxalyl chloride (300 µL, 3.4 mmol). The resulting solution was stirred for 24 hours at room temperature, concentrated by rotary evaporation, and allyl alcohol (15 mL) was added to the residue. The mixture was heated at 100° C. for 15 minutes and concentrated by rotary evaporation. The residue was purified by flash chromatography eluting with dichloromethane:methanol (95:5) to give the title compound as a solid (358 mg, 63% yield. 247–249° C.).

EXAMPLE 18

7-Chloro-3-(isopropoxycarbonyl)pyrazolo[3,4-c][1]benzazepine-4,10(1H,9H)-dione

A solution of 7-chloro-3-(ethoxycarbonyl)pyrazolo[3,4-c][1]benzazepine-4,10(1H,9H)-dione (500 mg, 1.56 mmol), 2-propanol (60 mL), and concentrated hydrochloric acid (3 drops) was subjected to three cycles of partial solvent removal by slow distillation (over 6 hours) followed by overnight reflux. After the third cycle, solvent was removed by rotary evaporation and the crude product was purified by flash chromatography eluting with dichloromethane:2-propanol (95:5–85:15) to yield the title compound as a white solid (256 mg, 48%, m.p. 291° C). Alternatively, the title compound can be prepared as described in Example 18 shown hereinbelow in Table 1.

EXAMPLE 19

7-Chloro-3-cyanopyrazolo[3,4-c][1]benzazepine-4,10(1H,9H)-dione

A solution of 7-chloro-3-(aminocarbonyl)pyrazolo[3,4-c[1]benzazepine-4,10(1H,9H)-dione (590 mg, 2.03 mmol)

(compound of Example 14) in phosphorous oxychloride (2.56 mL) was refluxed for 70 minutes. The excess phosphorous oxychloride was distilled off at atmospheric pressure and 106° C. To the remaining dark brown residue was added water (40 mL). The aqueous phase was extracted with ethyl acetate (4×50 mL). The organic layers were combined and dried over magnesium sulfate, filtered, and concentrated on a rotary evaporator to give the title compound as a broaqvgold solid (≈216 mg, 39% yield, m.p. 370° C. dec.).

EXAMPLE 20

(a) 1-(4-Methoxyphenylmethyl)-7-chloro-3-[(N-methoxy-N-methyl-amino)carbonyl]pyrazolo[3,4-c][1]benzazepine-4,10(1H,9H)-dione or 2-(4-Methoxyphenylmethyl)-7-chloro-3-[(N-methoxy-N-methylamino)carbonyl]-pyrazolo[3,4-c][1]benzazepine-4,10-(2H,9H)-dione To a solution of 7-chloro-3-[(N-methoxy-N-methylamino)carbonyl]pyrazolo[3,4-c][1]benzazepine-4,10 (1H,9H)-dione (1.7 g, 5.07 mmol) (compound of Example 8) at 0° C. was added N,N-dimethylformamide (25 mL) and sodium iodide (154 mg, 1.03 mmol). The solution was stirred at 0° C. for 10 minutes and sodium carbonate (639 mg, 6.03 mmol) and ethanol (17 µL) were added. The solution was stirred for 15 minutes and 4-methoxybenzyl chloride (811 mg, 5.18 mmol) was added. The solution was stirred at room temperature for 16 hours. The solution was quenched with saturated ammonium chloride (84 mL) and exhaustively extracted with ethyl acetate (10×40 mL). The organic layers were combined, dried over sodium sulfate, filtered, and concentrated by rotary evaporation to give a yellow oily solid. The crude material was purified by flash chromatography eluting with cyclohexane:ethyl acetate (90:10–70:30) to give one of the title compound regioisomers cleanly (1 g, 44%); $R_f$ 0.51 (1:1 ethyl acetate:hexane).

EXAMPLE 20

(b) 1-(4-Methoxyphenylmethyl)-7-chloro-3-formylpyrazolo3,4c][1]benzepine-4,10(1H,9H)-dione or 2-(4-methoxyphenylmethyl)-7-chloro-3-formylpyrazolo[3,4-c[1]benzazepine-4,10(2H,9H)-dione A solution of the single regioisomer from Example 20(a) above (955 mg, 2.10 mmol) in THF (48 mL) was cooled to −78° C. and diisobutylaluminum hydride in dichloromethane (14.7 mL, 14.7 mmol) was added. The solution was stirred at −78° C. for 165 minutes and then methanol (24 drops) and water (220 mL) were added. The aqueous layer was extracted with ethyl acetate (5×30 mL). The organic layers were combined, dried over anhydrous sodium sulfate, filtered and concentrated by rotary evaporation to give a crude solid (722 mg). The aqueous layer was allowed to stand for 17 hours and then re-extracted with ethyl acetate (2×200 mL). The organic layers were treated as described above. All crude material was combined to give a solid (772 mg. 81% crude yield).

To a solution of pyridine (1.80 mL, 22.8 mmol) in dichloromethane (17 mL) was added chromium (VI) oxide (1.15 g, 11.5 mmol) in two portions over 10 minutes. The resulting mixture was stirred for 30 minutes. To this solution was added the previously isolated solid (760 mg) and the solution was stirred for 24 hours. The dichloromethane solution was separated by decanting and the residue was washed with dichloromethane (5×50 mL). The combined organic layers were washed with 1N aqueous hydrochloric acid (187 mL). The aqueous extract was diluted with water (200 mL) and extracted with dichloromethane (5×200 mL) and ethyl acetate (3×200 mL). All organic layers were combined and filtered, partially concentrated by rotary evaporation, dried over anhydrous sodium sulfate, and concentrated by rotary evaporation to yield a light tan powder. This crude product was purified by flash chromatography eluting with chloroform:ethyl acetate (80:20) to give the title compound as a white solid (509 mg, 62%; $R_f$ 0.67, hexanes:ethyl acetate 1:1).

EXAMPLE 20

(c) 7-Chloro-3-formylpyrazolo[3,4-c][1]benzazepine-4,10(1H,9H)-dione

A solution of 1-(4-methoxyphenylmethyl)-7-chloro-3-formylpyrazolo[3,4-c][1]benzazepine-4,10(1H,9H)-dione or 2-(4-methoxyphenylmethyl)-7-chloro-3-formylpyrazolo [3,4-c][1]benzazepine-4,10(2H,9H)-dione from Example 20(b) above (400 mg, 1.01 mmol) and ceric ammonium nitrate (2.2 g, 4.03 mmol) in a mixture of acetonitrile (12 mL) and water (4 mL) was stirred for 17 hours at room temperature and filtered. The isolated solid was washed with a mixture of acetonitrile (12 mL) and water (4 mL) followed by acetone (10 mL). The acetonitrile-water solutions were extracted with ethyl acetate. The solid material from above was combined with the ethyl acetate extract and solvent was removed by rotary evaporation. The residue was washed with hot methanol (1×20 mL then 1×10 mL) and dried to give the title compound (25 mg, 9%).

EXAMPLE 2 1

(a) Ethyl 4-(4-chloro-2-nitrobenzoyl)-3-benzoyl-1H-pyrazole-5-carboxylate

A solution of ethyl 4-(4-chloro-2-nitrophenyl)-4-oxo-2-butynoate (prepared as described in Example 48(a)) (1.2 g, 4.11 mmol) and diazoacetophenone (1.2 g 8.22 mmol, prepared as described in *Org. Syn. Coll.* Vol. VI. pp. 386–388) in tetrahydrofiuran (THF) (21.6 mL) was stirred at room temperature for 16 hours. The reaction was concentrated by rotary evaporation and purified by flash chromatography eluting with hexanes:ethyl acetate (90:10, 80:20, 70:30) to give the title compound (1.3 g, 74.3%); $R_f$ 0.38 (1:1 ethyl acetate:hexanes).

(b) Ethyl 4-(4-chloro-2-aminobenzoyl)-3-benzoyl-1H-pyrazole-5-carboxylate

Following a procedure similar to that described in Example 23(d), ethyl 4-(4-chloro-2-nitrobenzoyl)-3-benzoyl-1H-pyrazole-5-carboxylate (1.2g 2.81 mmol) was treated with nickel boride to afford crude product. The crude product was purified by flash chromatography eluting with hexanes:ethyl acetate (75:25–50:50) to give the title compound as a solid (620 mg, 56%).

(c) 3-Benzoyl-7-chloropyrazolo[3,4-c][1]benzazepine-4,10(1H,9H)-dione

A solution of ethyl 4-(4-chloro-2-aminobenzoyl)-3-benzoyl-1H-pyrazole-5-carboxylate (620 mg, 1.56 mmol), 1-methyl-2-pyrrolidinone (4 mL) and ammonium acetate (120 mg, 1.56 mmol) was heated at 146° C. for 16.5 hours. The temperature was increased to 160° C. for 1 hour. The solution was allowed to cool to room temperature and water (60 mL) was added. The insoluble material (468 mg) was filtered, dried, and twice subjected to flash chromatography eluting with hexanes:ethyl acetate (90:10–50:50) to give impure product. The crude solid was triturated with ethanol (15 mL), washed with ethanol (3×10 mL) and dried to give the title compound (30.5 mg, 5.6% yield m.p. 370–373° C. dec.).

EXAMPLE 22

(a) N-benzyloxybenzylideneamine

To a mixture of ethanol (100 mL), potassium carbonate (8.98 g, 65 mmol), and O-benzylhydroxylamine hydrochloride (10.0 g, 62.7 mmol) was added benzaldehyde (6.65 g, 62.7 mmol). The mixture was refluxed for 5 hours, allowed to cool to room temperature, and diluted with water (500 mL). The aqueous solution was extracted with ethyl acetate (500 mL). The organic layer was washed with water, dried over magnesium sulfate, filtered, and concentrated by rotary evaporation to give the title compound as a yellow oil (14.96 g, 119%).

(b) N,O-Dibenzylhydroxylamine hydrochloride

To a solution of crude N-benzyloxybenzylideneamine from Example 22(a) (3.0 g, 14.2 mmol) in dichloromethane (30 mL) at 0° C. was added dimethylphenylsilane (3.09 mL, 20.3 mmol) followed by trifluoroacetic acid (3.92 mL, 50.6 mmol). The solution was allowed to warm to room temperature and was stirred for 16 hours. The solution was concentrated by rotary evaporation. To the crude oil was added dichloromethane (20 mL) and a hydrogen chloride saturated solution of dichloromethane (20 mL). The insoluble material (300 mg) was filtered and the solution was concentrated by rotary evaporation. To the crude oil was added a hydrogen chloride saturated solution of ether (20 mL). Additional ether (100 mL) was added and the insoluble material was filtered. The solid obtained was combined with the initial solid filtered above to give the title compound (1.57 g, 45%).

(c) 7-Chloro-3-[(N-hydroxy-N-benzylamino) carbonyl]pyrazolo[3,4-c][1]benzazepine-4,10(1H, 9H)-dione A solution of 7-chloro-3-(carboxy)pyrazolo[3,4-c][1] benzazepine-4,10(1H,9H)-dione (459 mg, 1.7 mmol) (compound of Example 9) and 1,1'-carbonyldiimidazole (421 mg, 2.6 mmol) in N,N-dimethylformamide (3 mL) was heated at 50° C. for 1 hour. In one portion N,O-dibenzylhydroxylamine hydrochloride (1.3 mg, 5.24 mmol) was added and the solution was heated at 50° C. for 1 hour. The reaction was cooled to room temperature and water (35 mL) was added. The aqueous layer was extracted with ethyl acetate (3×100 mL). The organic layers were concentrated by rotary evaporation to a volume of 15 mL and the insoluble material was filtered. The organic layer was concentrated by rotary evaporation and to the residue was added methanol (10 mL). The insoluble material was filtered and all solids were combined and dried to give a white solid (500 mg). To this solid was slowly added 10% aqueous sodium hydroxide (10–13 mL) until pH 11 was achieved. The insoluble material was removed by filtration and to the basic solution was added concentrated glacial acetic acid (3–4 mL) until a solid precipitated out. The insoluble material was filtered and dried to give the title compound (259 mg, 40.3%, m.p. 282–285° C.).

EXAMPLE 23

(a) 2,2,2-Trifluorodiazoethane

To a solution of 3,3,3-trifluoroethylamine hydrochloride (14.8 g, 109 mmol) in water (55 mL) was added diethyl ether (82 mL) followed by sodium nitrite (8.2 g, 119 mmol). The reaction was sealed with a TEFLON™ stopper and stirred at room temperature for 3 hours. The layers were separated and the volume of the ether layer was measured to be 82 mL. The trifluorodiazoethane concentration of the ether solution was determined to be 0.7M as described below, for a yield of 52.5% (6.31 g) of 2,2,2-trifluorodiazoethane.

A 1.00 mL aliquot of ethereal trifluorodiazoethane was added to a vigorously stirred solution of excess p-toluenesulfonic acid monohydrate (510 mg, 2.68 mmol) in diethyl ether (10 mL). Water (10 mL) was added, followed by a few drops of phenolphthalein indicator. The mixture was titrated to a pink end point with 0.2N aqueous sodium hydroxide solution (9.9 mL), demonstrating that 0.7 mmol of p-toluenesulfonic acid had been consumed by reaction with 2,2,2-trifluorodiazoethane.

(b) Ethyl 3-trifluoromethyl-4-[(4-chloro-2-nitrophenyl)(hydroxy)methyl]1H-pyrazole-5-carboxylate The ethereal 2,2,2-trifluorodiazoethane solution (80 mL, 56 mmol) from Example 23(a) above was added to ethyl 4-(4-chloro-2-nitrophenyl)-4-hydroxy-2-butynoate (3.09 g, 10.9 mmol) and the solution was stirred at room temperature for 3 days. TLC showed traces of remaining starting material ($R_f$ 0.67, 1:1 ethyl acetate:hexanes) and two new products ($R_f$ 0.36, 0.48). Excess 2,2,2-trifluorodiazoethane was quenched by slow addition of a solution of p-toluenesulfonic acid in diethyl ether.

This sequence (Examples 23(a) and (b)) was repeated exactly as described above (in the second run the 2,2,2-trifluorodiazoethane concentration was determined to be 0.54M, for a yield of 4.78 g, 40%) and the resulting diethyl ether solutions were combined, washed with water (1×50 mL then 2×75 mL) and saturated aqueous sodium chloride (1×75 mL), dried over anhydrous sodium sulfate, filtered, and concentrated to give an orange-red oil (20 g). This material was purified by flash chromatography (hexane:ethyl acetate; 90:10 then 80:20) to give pure title compound (2.39 g, 28%) and a mixture of regioisomers (0.88 g).

(c) Ethyl 4-(4-chloro-2-nitrobenzoyl)-3-trifluoromethyl-1H-pyrazole-5-carboxylate Chromium(VI) oxide ($CrO_3$, 2.828 g, 28.28 mmol) was added to a solution of pyridine (4.58 mL, 56.63 mmol) in dichloromethane (70 mL) and the mixture was stirred at room temperature for 15 minutes. To the resulting burgundy-colored solution was added a solution of ethyl 3-trifluoromethyl-4-[(4-chloro-2-nitro-phenyl)(hydroxy) methyl]-1H-pyrazole-5-carboxylate (1.64 g, 4.17 mmol) in dichloromethane (15 mL). The resulting mixture was stirred at room temperature for 4 days. The dichloromethane solution was decanted from the dark viscous residue, which was washed with diethyl ether (3×100 mL). The dichloromethane and diethyl ether extracts were combined, washed successively with 1N aqueous hydrochloric acid (2×100 mL) and saturated aqueous sodium chloride, dried over anhydrous magnesium sulfate, filtered, and concentrated by rotary evaporation to afford 1.33 g (82%) of the title compound as a yellow solid.

(d) Ethyl 4(4-chloro-2-aminobenzoyl)-3-trifluoromethyl-1H-pyrazole-5-carboxylate Nickel boride ($Ni_2B$, PYROPHORIC) was generated by slow addition (over 15 minutes, so that the internal temperature remained between 10° C. and 16° C.) of a (cloudy) solution of sodium borohydride (NaBH$_4$, 1.22 g, 32.25 mmol) in water (16 mL) to a cooled (to 10° C. using an ice water bath) solution of nickel(II) acetate tetrahydrate [Ni(OAc)$_2$·4H$_2$O] (2.02 g, 8.12 mmol) in water (30 mL). A granular black precipitate formed immediately as the sodium borohydride solution was added. After completion of the addition the mixture was stirred at 10–15° C. for 2 hours. The black precipitate was separated by vacuum filtration through a medium frit under a nitrogen atmosphere provided by blowing nitrogen through an inverted funnel suspended above the filtration. The black precipitate was washed with water (3×10 mL) and ethanol (3×10 mL), giving 1.06 g of a fine black powder. This material was used immediately for the following reaction; use of material which had been stored overnight gave unsatisfactory results.

The freshly prepared nickel boride (1.06 g) was added to a solution of ethyl 4-(4-chloro-2-nitrobenzoyl)-3-trifluoromethyl-1H-pyrazole-5-carboxylate (437.0 mg, 1.116 mmol) in ethanol (20 mL) followed by addition of 1.0N aqueous hydrochloric acid (5.0 mL). This mixture was stirred at 60° C. for 30 minutes and then at room temperature overnight ( 17 hours). The reaction mixture was poured into water (250 mL) and extracted with diethyl ether (2×250 mL). The organic extract was filtered to remove residual black solids, washed successively with water (250 mL) and saturated aqueous sodium chloride (250 mL), dried over anhydrous magnesium sulfate, filtered, and concentrated by rotary evaporation to afford 0.42 g of greenish-yellow solid. This material was dissolved in ethyl acetate (50 mL) and preabsorbed onto 4.1 g of silica gel, which was then applied to the top of a 40 g (2.84×14.2 cm) silica gel flash chromatography column. The column was eluted with hexane-ethyl acetate (90:10 then 80:20) to give 235.6 mg (58.41%) of the title compound as a light yellow solid.

(e) 7-Chloro-3-trifluoromethylpyrazolo[3,4-c][1]benzazepine-4,10(1H,9H)-dione

To a solution of ethyl 4-(4-chloro-2-aminobenzoyl)-3-trifluoromethyl-1H-pyrazole-5-carboxylate (360 mg, 0.997 mmol) in toluene (50 mL) was added 2-hydroxypyridine (93.9 mg, 0.988 mmol). Toluene was removed by distillation and the residue was heated at 170° C. for 2 days. The flask was cooled to room temperature and dichloromethane (20 mL) was added. The insoluble material was filtered to give crude solid (284 mg). The crude material was continuously chromatographed eluting with dichloromethane (100 mL) and dichloromethane:2-propanol (98:2, 200 mL). The fractions were concentrated bv rotary evaporation and were found to contain a contaminant from tygon tubing. The fractions were combined and flash chromatographed through a plug of silica gel to remove the contaminant, eluting with hexanes, hexanes:ethyl acetate (95:5, 90:10), dichloromethane, and dichloromethane:2-propanol (95:5, 90:10). The product fractions were concentrated by rotary evaporation to give the title compound as a white solid (124 mg, 37%. m.p. 337–339° C.).

Alternatively, the title compound can be preferably prepared as follows: A mixture of ethyl 4-(4-chloro-2-aminobenzoyl)-3-trifluoromethyl-1H-pyrazole-5-carboxylate (1.0 g, 2.76 mmol), ammonium acetate (0.21 g, 2.76 mmol) and 1-methyl-2-pyrrolidinone (2.3 mL) was heated with stirring at 160° C. under N$_2$ for one hour. After cooling to room temperature, water (25 mL) was added to the stirred reaction mixture. The resulting aqueous mixture was filtered after stirring for ten minutes. The filter cake was washed with water (2×25 mL) then dried under vacuum to give a tan solid. The solid was placed in methylene chloride (25 mL) and the mixture was stirred for fifteen minutes, then filtered. The filter cake was washed with methylene chloride (2×25 mL) and dried under vacuum to give the title compound as a tan solid (0.66 g, 76%, m.p. 334–336° C.).

EXAMPLE 24

7-Chloro-3-[(N-phenyl-N-methylamino)carbonyl]pyrazolo[3,4-c][1]benzazepine-4,10(1H,9H)-dione To a suspension of 7-chloro-3-(carboxy)pyrazolo[3,4c][1]-benzazepine-4,10(1H,9H)-dione (500 mg, 1.72 mmol) (compound of Example 9) in carbon tetrachloride (5 mL) was added phosphorus pentachloride (358 mg, 1.72 mmol). The mixture was stirred for 17 hours, filtered and washed with carbon tetrachloride (3×10 mL). To the residue was added N-methylaniline (190 μL, 1.72 mmol) and dioxane (7 mL). The resulting mixture was stirred 17 hours. To this mixture was added water (50 mL). The aqueous layer was separated and extracted with ethyl acetate (3×100 mL). The organic layers were combined and concentrated by rotary evaporation to 50 mL. The insoluble material was removed by filtration and the organic solution was preabsorbed onto silica gel and purified by flash chromatography eluting with chloroform and chloroform:2-propanol (99:1, 98:2–90:10). The product fractions were combined and concentrated by rotarv evaporation to give the title compound as a light yellow solid (100 mg, 15.2%, m.p. 308° C.).

EXAMPLE 25

(a) Benzaldehyde Tosylhydrazone

To a slurry of p-toluenesulfonylhydrazide (1.05 g, 5.63 mmol) in absolute methanol (5 mL) was added freshly distilled benzaldehyde (0.5g, 4.7 mmol). The p-tosyhydrazide dissolved giving a clear solution. Within 7–10 minutes of stirring at room temperature, the title compound began to crystallize. The reaction mixture was cooled to −15° C. for 5 minutes. The solid was filtered, washed with 15 mL of cold methanol and dried under aspirator vacuum to yield off-white crystals of the title compound (1.31 g, 100%, m.p. 135.5–136.1° C.).

(b) Phenyldiazomethane

In an oven-dried round bottom flask was placed benzaldehyde tosylhydrazone (1.15 g, 4.2 mmol), followed by 4.3 mL of a 1.0M solution of sodium methoxide in methanol (2.3 g Na metal dissolved in absolute methanol and diluted to 100 mL). The mixture was swirled until all the contents dissolved. Most of the solvent was removed via romy evaporation and the last traces of solvent by evacuation of the flask under high vacuum for 2 hours. The solid obtained was subjected to a Kugelrohr distillation at 215° C. and 200 millitorr for 1 hour. At 68–70° C., the title compound, as a red oil, was collected in a receiver flask in a quantitative yield.

(c) Ethyl 3-phenyl-4-[(4-chloro-2-nitrophenyl)(hydroxy)methyl-1-H-pyrazole-5-carboxylate A solution of freshly generated phenyldiazomethane (2.44 g, 20.7 mmol) in 10 mL of anhydrous THF was added to ethyl 4-(4-chloro-2-nitrophenyl)-4-hydroxy-2-butynoate (5.86 g, 20.7 mmol) in 10 mL THF and the mixture was stirred at room temperature for 18 hours. The reaction mixture was quenched with excess ethereal acetic acid and concentrated via rotary evaporation to an oil (12.24 g) which solidified on cooling. This was filtered to yield the title compound as a pale yellow solid (2.42 g). The filtrate was concentrated via rotary evaporation to an oil which was triturated with hexane:ethyl acetate (4:1) to yield an additional 1.52 g of the title compound (48% combined yield).

(d) Ethyl 3-phenyl-4-(4-chloro-2-nitrobenzoyl)-1H-pyrazole-5-carboxylate

To a solution of dry pyridine (0.237 g, 300 mmol) in anhydrous methylene chloride (5 mL) was slowly added chromium trioxide (0.15 g, 1.5 mmol) to give a wine colored mixture which was stirred at room temperature for 10 minutes. A solution of ethyl 3-phenyl4[(4-chloro-2-nitrophenyl)-(hydroxy)methyl]-1H-pyrazole-5-carboxylate (0.10 g, 0.25 mmol) in anhydrous methylene chloride (2 mL) was added to the wine red mixture in three portions over 25 minutes. The reaction mixture was stirred at room temperature for 18 hours. The reaction mixture was filtered and the filtrate extracted with 3×20 mL 3N HCl. The combined organic extracts were dried with sodium sulfate and concentrated via rotary evaporation to give an oil (0.1 g) which was triturated with hexane:ethyl acetate (4:1) to give the title compound as a tan solid (0.075 g, 75%).

(e) Nickel Boride

A mixture of nickel(II) acetate tetrahydrate (2.0 g, 8.0 mmol) in water (30 mL) was stirred at room temperature to produce a green solution which was cooled to 0° C. Sodium borohydride (1.21 g, 32 mmol) in water (16 mL) was added dropwise over 30 minutes via pipet to the green solution maintaining the temperature at 11–12° C. The resulting black slurry was filtered, washed with water (3×25 mL) and ethanol (3×10 mL) and dried under aspirator vacuum and a blanket of $N_2$, taking care to not dry the solid too much as it may ignite. Yield of wet, black solid recovered (0.82 g, 1.37×theoretical yield).

(f) Ethyl 3-phenyl-4-(4-chloro-2-aminobenzoyl)-1H-pyrazole-5-carboxylate

A suspension of nickel boride (3.56 g) and 1N HCl (16 mL) in methanol (65 mL) was added to ethyl 3-phenyl-4-(4-chloro-2-nitrobenzoyl)-1H-pyrazole-5-carboxylate (1.5 g, 3.7 mmol) and the mixture heated to 60° C. for 18 hours. The reaction mixture was filtered and the filtrate concentrated via rotovap to a green solid (2.38 g). The solid was dissolved in ethyl acetate (100 mL) and extracted with water (2×50 mL) and brine (1×50 mL). The organic layer was dried over sodium sulfate and concentrated to a dark green oil (1.5 g) which was washed with a small amount of hexanes to yield the title compound as a yellow solid (0.855 g, 62%).

(g) 7-Chloro-3-phenylpyrazolo[3,4-c][1]benzazepine-4,10(1H,9H)-dione

A mixture of ethyl 3-phenyl-4-(4-chloro-2-aminobenzoyl)-1H-pyrazole-5-carboxylate (0.84 g, 2.28 mmol) and 2-hydroxy-pyridine (0.217 g, 2.28 mmol) in toluene (12 mL) was distilled at 160° C. until all the toluene was removed. The residue was heated at the same temperature for 18 hours. The reaction residue was washed with water to remove the 2-hydroxy-pyridine. The insoluble material was added to methanol (225 mL) and heated to boiling. Ethyl acetate (100 mL) was added and the solution heated for an additional 2 minutes, then concentrated to 100 mL. The solution was filtered to remove some insoluble material and the filtrate concentrated via rotovap until a precipitate formed which was filtered to give the title compound as a tan solid (0.381 g, 51%, mp 328.1–330.9° C.).

Various other compounds of the Formula I, wherein X is O and C is a pyrazole ring, were prepared utilizing the procedures described in general procedures A, B and C and are illustrated in Table 1.

GENERAL PROCEDURES

PROCEDURE A

To an oven-dried flask was added 7-chloro-3-(ethoxycarbonyl)pyrazolo[3,4-c][1]benzazepine-4,10(1H, 9H)-dione (0.50 g, 1.58 mmol) and an appropriate alcohol of the Formula IV ($R^5OH$) (10 mL). To the resulting slurry was added titanium (IV) isopropoxide (0.89 g, 3.14 mmol) via syringe and the mixture was heated to reflux for 10–90 minutes. The reaction mixture was quenched with 1N HCl (20 mL). Ether (30 mL) was added and any insoluble material was removed by filtration. The filtrate was extracted with ether (3×30 mL). The combined organic extracts were dried over $Na_2SO_4$ and concentrated via rotary evaporator to give the crude product. The solid was recrystallized from methanol to afford the compounds of the formula I which are listed in Table 1.

PROCEDURE B (a) Preparation of catalyst for Procedure B Di-n-butyltin diisothiocyanate Di-n-butyltin oxide (3.36 g, 13.5 mmol) and ammonium thiocyanate (2.05 g, 27.0 mmol) were suspended in methylcyclohexane (125 mL) in a flask equipped with a nitrogen gas inlet and a Dean-Stark trap. The reaction mixture was slowly heated to reflux with vigorous stirring and refluxed for 18 hours. Methylcyclohexane (100 mL) was removed via rotary evaporator and an insoluble mass settled. Chloroform (80 mL) was added and the mixture heated to boiling, then filtered to remove unreacted ammoni un thiocyanate. The filtrate which had begun to crystallize was concentrated to 50 mL under a stream of nitrogen and filtered to give an off-white solid. Recrystallization from methylene chloride gave the title compound as a white solid (2.13 g, 45%, mp 151° C.).

1-Hydroxy-3-(isothiocyanato)-tetrabutyldistannoxane

A mixture of di-n-butyltin oxide (2.14 g, 8.6 mmol) and di-n-butyltin diisothiocyanate (1.0 g, 2.8 mmol) in ethanol (30 mL) was heated to reflux for 6 hours during which time the white slurry became a clear solution. The reaction mixture was concentrated via rotary evaporator to a solid which was pulverized and left exposed at ambient temperature for 18 hours. The powder was recrystallized from hexanes at 0° C. to give the title compound as a white solid (2.74 g, 86%).

(b) The Procedure

A toluene solution (10 mL) of 7-chloro-3-(ethoxycarbonyl)pyrazolo[3,4-c][1](benzazepine-4,10(1H,9H)-dione (0.50 g, 1.58 mmol), an appropriate alcohol of the Formula IV ($R^5OH$) (15.8 mmol) and 1-hydroxy-3-(isothiocyanato)tetrabutyl-distannoxane (0.176 g, 0.316 mmol) was heated at reflux for 18 hours. The reaction mixture was concentrated via rotary evaporator to give an impure solid. This solid was subjected to flash chromatography using hexane:ethyl acetate (95:5) as the eluent to remove the tin catalyst and methylene chloride:methanol (50:50) to recover the product, which was further purified by recrystallization from methanol to afford the compounds of the Formula I which are listed in Table 1.

PROCEDURE C

To a flame-dried flask was added 7-chloro-3-(carboxy) pyrazolo[3,4-c][1]benzazepine-4,10(1H,9H)-dione (0.50 g, 1.7 mmol) (compound of Example 9) and anhydrous methylene chloride (10 mL). To the resulting slurry was added oxalyl is chloride (0.43 g, 3.4 mmol) and anhydrous dimethylformamide (2 drops) and the reaction mixture was stirred at room temperature for 1 hour. An aliquot of the reaction mixture was quenched with methanol to check for complete formation of the methyl ester which indicated that formation of the acid chloride was complete. The reaction mixture was concentrated via rotary evaporator and immediately treated with an appropriate alcohol of the formula IV ($R^5OH$) (5–10 mL) at 100° C. for 15 minutes. The slurry was filtered and washed with water to recover the crude product. Any precipitated solid in the filtrate was recovered and combined with the previous solid. The combined solids were recrystallized from methanol to afford the compounds of the formula I which are listed in Table 1.

mL) was added anhydrous hydrazine (0.14 g, 4.5 mmol) dropwise via syringe. The resulting bright yellow mixture immediately darkened to an orange color. After 45 minutes of stirring at room temperature, the reaction mixture became a thick yellow-orange slurry which was allowed to stir for an additional 18 hours. The reaction mixture was filtered to give a solid which was recrystallized from ethanol. Very little product was recovered and the filtrate was concentrated and purified with a silica gel plug using ethyl acetate:hexanes (50:50) as the eluent to give an orange oil. This was allowed to crystallize in ethanol at –10° C. for 18 hours, filtered and dried at 100° C. to give the title compound (0.2 g, 25%, m.p. 226.5–228.6° C.).

EXAMPLE 46

7-Chloro-3-(carboxymethyl)pyrazolo[3,4-][1] benzazepine-4,10(1H,9H)-dione

To a mixture of 7-chloro-3-((t-butoxy)carbonylmethyl) pyrazolo[3,4-c][1]benzazepine-4,10(1H,9H)-dione (0.26 g, 0.72 mmol) in methylene chloride (6 mL) was added trifluoroacetic acid (6.38 g, 56 mmol) via syringe. The reaction was stirred at room temperature for 30 minutes. The reaction

TABLE I

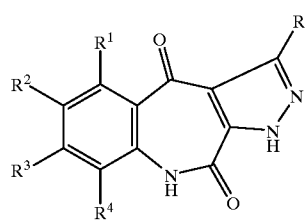

| Example No. | $R^1$ | $R^2$ | $R^3$ | $R^4$ | R | Alcohol of the Formula IV ($R^5OH$) | Procedure | Yield | m.p. ° C. |
|---|---|---|---|---|---|---|---|---|---|
| 18 | H | H | Cl | H | —C(O)OCH($CH_3$)$_2$ | HOCH($CH_3$)$_2$ | A | 80 | 301 |
| 26[a] | H | H | Cl | H | —C(O)OCH($CH_3$)Et | HOCH($CH_3$)Et | A | 40 | 287.8–289.5 |
| 27[a] | H | H | Cl | H | —C(O)O($CH_2$)$_3$$CH_3$ | HO($CH_2$)$_3$$CH_3$ | A | 60 | 259.5–261.1 |
| 28[a] | H | H | Cl | H | —C(O)O($CH_2$)$_2$$CH_3$ | HO($CH_2$)$_2$$CH_3$ | A | 61 | 272.6–273.3 |
| 29[a] | H | H | Cl | H | —C(O)O($CH_2$)$_2$Ph | HO($CH_2$)$_2$Ph | A | 56 | 227.6 |
| 30[a] | H | H | Cl | H | —C(O)OCH$_2$CH($CH_3$)$_2$ | HOCH$_2$CH($CH_3$)$_2$ | A | 76 | 282.7–283.6 |
| 31[a] | H | H | Cl | H | —C(O)O($CH_2$)$_3$Ph | HO($CH_2$)$_3$Ph | A | 87 | 225.6–227.5 |
| 32[a] | H | H | Cl | H | —C(O)O($CH_2$)$_2$CH=$CH_2$ | HO($CH_2$)$_2$CH=$CH_2$ | A | 62 | 250.9–251.3 |
| 33[b] | H | H | Cl | H | —C(O)OCH$_2$cyclopropyl | HOCH$_2$cyclopropyl | B | 57 | 269.4–269.6 |
| 34[a] | H | H | Cl | H | —C(O)O($CH_2$)$_3$CH=$CH_2$ | HO($CH_2$)$_3$CH=$CH_2$ | A | 75 | 231.3–233.4 |
| 35[a] | H | H | Cl | H | —C(O)OCH($CH_3$)$CH_2$CH=$CH_2$ | HOCH($CH_3$)$CH_2$CH=$CH_2$ | A | 55 | 242.9–244.1 |
| 36 | H | H | Cl | H | —C(O)O($CH_2$)$_2$$SCH_3$ | HO($CH_2$)$_2$$SCH_3$ | C | 63 | 230.9–233.1 |
| 37 | H | H | Cl | H | —C(O)O($CH_2$)$_2$C($CH_3$)=$CH_2$ | HO($CH_2$)$_2$C($CH_3$)=$CH_2$ | C | 22 | 234.9–236.2 |
| 38 | H | H | Cl | H | —C(O)OCH$_3$ | HOCH$_3$ | C | 73 | 302.6 dec. |
| 39 | H | H | Cl | H | —C(O)O($CH_2$)$_2$C≡CH | HO($CH_2$)$_2$C≡CH | C | 21 | 255–255.6 |
| 40 | H | H | Cl | H | —C(O)O($CH_2$)$_3$$SCH_3$ | HO($CH_2$)$_3$$SCH_3$ | C | 60 | 212.9 |
| 41 | H | H | Cl | H | —C(O)O($CH_2$)$_3$Cl | HO($CH_2$)$_3$Cl | C | 26 | 228.9–229.6 |
| 42 | H | H | Cl | H | —C(O)O($CH_2$)$_2$Cl | HO($CH_2$)$_2$Cl | C | 30 | 254.9–255.1 |
| 43[c] | H | H | Cl | H | —C(O)OCH$_2$$CF_3$ | HOCH$_2$$CF_3$ | C | 23 | 249.1–256.4 |
| 44 | H | H | Cl | H | —C(O)OCH$_2$C≡C—Ph | HOCH$_2$C≡C—Ph | C | 24 | 231.0–233.1 |

[a]contains a small amount (generally less than 10%) of the corresponding isopropyl ester as an impurity.
[b]contains a small amount (less than 10%) of the corresponding ethyl ester starting material as an impurity.
[c]0.2 equivalents of dimethylaminopyridine (DMAP) was also added to the reaction mixture.

EXAMPLE 45

7-Chloro-3-((t-butoxy)carbonylmethyl)pyrazolo-[3,4-c][1-benzazepine-4,10(1H,9H)-dione To a slurry of t-butyl(E)-3-(8-chloro-3-methoxy-2,5-dioxo-2,5-dihydro-1H-benz[b]azepin-4-yl)acrylate (prepared as described in Example 44 of WO94/29275 published Dec. 22, 1994) (0.81 g, 2.2 mmol) in methanol (5 mixture was concentrated via rotary evaporator to give a solid which was recrystallized from dimethylformamide and dried at 100° C. to yield the title compound (0.14 g, 64%, mp 297.3–299.6° C.).

EXAMPLE 47

7-Chloro-3-(ethoxycarbonyl)-10-thioxopyrazolo[3,4-c][1]benzazepine-4(1H,9H)-one

To a suspension of Lawesson's Reagent [(2,4-bis(4-methoxyphenyl)-1,3-dithia-2,4-diphosphetane-2,4- disulfide)(0.32 g, 0.80 mmol) in dry toluene (15 mL) at room temperature was added 7-chloro-3-(ethoxycarbonyl) pyrazolo-[3,4-c][1]benzazepine-4,10(1H,9H)-dione (0.51 g, 1.59 mmol) in one portion. The resulting slurry was heated to reflux for 1.5 hours. The reaction mixture was filtered to remove insoluble material. The filtrate was concentrated via rotary evaporator to give a green oil which was purified by flash chromatography using chloroform:methanol (9:1) as the eluent. The yellow-green solid recovered was recrystallized from methanol to give the title compound (0.44 g, 82%, mp 248.0–252.6° C.).

EXAMPLE 48

(a) Ethyl 4-(4-chloro-2-nitrophenyl)-4-oxo-2-butynoate

To a solution of ethyl 4-(4-chloro-2-nitrophenyl)-4-hydroxy-2-butynoate (7.46 g, 26.3 mmoles) in dichloromethane (350 mL) cooled in an ice-bath was added manganese dioxide (26.2 g, 301.3 mmol). The reaction mixture was stirred for 20 minutes and then was allowed to warm to room temperature. The reaction mixture was stirred at room temperature for 130 minutes and then was filtered twice through a pad of CELITE™. The filtrate was purified by flash chromatography on silica gel (195 g), eluting with dichloromethane, to afford 3.80 g (51%) of the title compound as a brownish-orange oil.

(b) Ethyl 4-(4-chloro-2-nitrobenzoyl)-1H-1,2,3-triazole-5-carboxylate

A solution of ethyl 4-(4-chloro-2-nitrophenyl)-4-oxo-2-butynoate (3.75 g, 13.31 mmol) in dimethylformamide (20 mL) was added dropwise to an ice-cooled solution of NaN₃ (901 mg, 13.86 mmol) in dimethylformamide (20 mL). The reaction mixture was stirred at ice-bath temperature for 3.25 hours and then the solvent was removed in vacuum (0.3 torr) overnight. The brown solid residue was suspended in water (400 mL) and acidified with concentrated hydrochloride acid (2 mL) to pH 1. The mixture was extracted with ether (2×400 mL) and the extracts were combined, washed with 1N HCl (100 mL), dried over MgSO₄, filtered and concentrated in vacuo (0.4 torr) to afford 3.96 (92%) of crude title compound as a brownish-orange solid. The crude product was recrystallized from refluxing toluene (100 mL) to afford 1.98 g (46%) of the title compound as pale greenish tan plates.

(c) Ethyl 4-(4-chloro-2-aminobenzoyl)-1H-1,2,3-triazole-5-carboxylate

A suspension of PtO₂ (541.6 mg) in ethanol (50 mL) was shaken under hydrogen (40 psi) in a PARR™ hydrogenator for 19 hours. A solution of ethyl 4-(4-chloro-2-nitrobenzoyl)-1H-1,2,3-triazole-5-carboxylate (1.014 g, 3.124 mmol) in chloroform (10 mL)/ethanol (200 mL) was then added to the reaction mixture and shaking on the PARR™ hydrogenator at 51 psi was continued. After 3 hours the reaction mixture was filtered through a pad of CELITE™, washing with ethanol. The filtrate was concentrated under vacuum (0.3 torr) to afford 0.998 g (108%) of crude title compound as a bright yellow foam.

(d) 7-Chloro-1,2,3-triazolo[4,5-c][1]benzazepine-4,10(1H,9H)-dione

A mixture of tetrahydrofuran (15 mL), ethyl 4-(4chloro-2-aminobenzoyl)-1H-1,2,3-triazole-5-carboxylate (844.1 mg, 2.86 mmol) and potassium t-butoxide (917 mg, 8.17 mmol) was stirred at 50–55° C. under argon for 75 minutes. Additional tetrahydrofuran (15 mL) was then added and stirring was continued for another 3.5 hours. The reaction mixture was quenched with acetic acid (500 µL, 8.73 mmol), followed by water (25 mL) and then was stirred at room temperature overnight. The product was collected by filtration, washed with water (10 mL) and then ether (5 mL) to afford, after drying in vacuo (0.2 torr) at 60° C., 228.9 mg (32%) of crude title compound as a light tan powder. The aqueous filtrate was refiltered to afford an additional 174.1 mg (24%) of the title compound. The title compound (194.5 mg) was purified by dissolving the compound in a mixture of saturated aqueous NAHCO₃ (1.0 mL), saturated aqueous Na₂CO₃ (1.0 mL) and water (100 mL) with heating (60° C.) and sonication and then acidifying the hot mixture with 3N HCl to a pH of about 2. A white precipitate formed which was collected by filtration and dried in vacuo (0.3 torr) at 60° C. to afford 154.1 mg (21.6%) of the title compound, m.p. 385–388° C.

EXAMPLE 49

(a) Ethyl 4-(5-chloro-2-nitrophenyl)-4-hydroxy-2-butynoate

To a solution of ethyl propiolate (4.05 mL, 40 mmol) in tetrahydrofuran (125 mL) at −78° C. under nitrogen was added n-BuLi (2.5 mL, 40 mmol, 1.6M in hexane). The reaction mixture was stirred at about −70° C. for 0.5 hours and then 2-nitro-5-chlorobenzaldehyde (6.75 g, 36.4 mmol) was added dropwise. The reaction mixture was stirred at −78° C. for 0.25 hours, warmed to −60° C., quenched with acetic acid (5 mL) and then warmed to room temperature. The reaction mixture was partitioned between ether (250 mL) and water (250 mL). The layers were separated and the organic layer was washed with brine (250 mL) and dried over Na₂SO₄. The mixture was filtered and the filtrate was concentrated in vacuo. The residue was purified by flash chromatography eluting with hexane/ethyl acetate (4:1) to afford 6.12 g (59%) of the title compound as a yellow oil which solidified on standing.

(b) Ethyl 4-(5-chloro-2-nitrophenyl)-4-oxo-2-butynoate

Following a procedure substantially similar to that described in Example 48(a), the is title compound (2.28 g, 38%) was obtained from ethyl 4-(5-chloro-2-nitrophenyl)-4-hydroxy-2-butynoate (6.12 g, 21.6 mmol), MnO₂ (24.0 g, 276 mmol) and CH₂Cl₂ (350 mL). The title compound was purified by flash chromatography eluting with hexane:ethyl acetate (4:1).

(c) Ethyl 4-(5-chloro-2-nitrobenzoyl)-1H-1,2,3-triazole-5-carboxylate

Following a procedure substantially similar to that described in Example 48(b), the title compound (1.474 g, 69%, as an off-white powder) was obtained from ethyl 4-(5-chloro-2-nitrophenyl)-4-oxo-2-butynoate (1.85 g, 6.6 mmol), NaN₃ (0.45 g, 6.9 mmol) and dimethylformamide (60 mL). The title compound was purified by recrystallization from hot hexane:ethylacetate (2:1, 50 mL).

(d) Ethyl 4-(5-chloro-2-aminobenzoyl)-1H-1,2,3-triazole-5-carboxylate

Following a procedure substantially similar to the procedure described in Example 48(c), the title compound (0.211 g crude) was obtained from ethyl 4-(5-chloro-2

-nitrobenzoyl)-1H-1,2,3-triazole-5-carboxylate (0.19 g, 0.6 mmol), PtO$_2$ (0.10 g), ethanol (65 mL) and chloroform (5 mL).

(e) 6-Chloro-1,2,3-triazolo[4,5-c][1]benzazepine-4,10(1H,9H)dione

Following a procedure substantially similar to that described in Example 48(d), the title compound (0.304 g, 59%, m.p. >250° C., as an off-white powder) was obtained (after drying in vacuo at 80° C.) from ethyl 4-(5-chloro-2-amino-benzoyl)-1H-1,2,3-triazole-5-carboxylate (0.61 g, 2.1 mmol) potassium t-butoxide (0.673 g, 6.0 mmol) and tetrahydrofuran (30 mL).

EXAMPLE 50

(a) Ethyl 4-(6-chloro-2-nitrophenyl)-4-hydroxy-2-butynoate

Following a procedure substantially similar to that described in Example 49(a), the title compound (6.44 g, 76%, brown-red oil) was obtained, after purification by flash chromatography eluting with hexane/ethyl acetate (5:1 to 3:1), from ethyl propiolate (3.3 mL 33 mmol), tetrahydrofuran (130 mL), n-BuLi (21 mL, 33 mmol, 1.6M in hexane) and 2-nitro-6-chlorobenzaldehyde (5.6 g, 30 mmol).

(b) Ethyl 4-(6-chloro-2-nitrophenyl)-4-oxo-2-butynoate

Following a procedure substantially similar to that described in Example 49(b), the title compound (4.36 g, 68%, yellow oil) was obtained, after purification by flash chromatography eluting with hexane:ethyl acetate (3:1), from ethyl 4-6-chloro-2-nitrophenyl)-4-hydroxy-2-butynoate (6.44 g, 22.0 mmol), MnO$_2$ (23.7 g, 273 mmol) and dichloromethane (360 mL).

(c) Ethyl 4-(6-chloro-2-nitrobenzoyl)-1H-1,2,3-triazole-5-carboxylate

Following a procedure similar to that described in Example 49(c), the title compound (3.79 g, 87%, orange solid) was obtained from ethyl 4-(6-chloro-2-nitrophenyl)-4oxo-2-butynoate (3.8 g, 13.5 mmol), NaN$_3$ (0.92 g, 14.2 mmol) and dimethylformamide (100 mL).

(d) Ethyl 4-(6-chloro-2-aminobenzoyl)-1H-1,2,3-triazole-5-carboxylate

Following a procedure substantially similar to that described in Example 49(d), the title compound (0.7823 g, 86%, yellow powder) was obtained, after purification by flash chromatography eluting with toluene/methanol/CH$_3$CO$_2$H (80:20:1), followed by trituration with hexane:ether (1:1, 30 mL), from ethyl 4-(6-chloro-2-nitrobenzoyl)-1H-1,2,3-triazole-5-carboxylate (1.0 g, 3.1 mmol), PtO$_2$ (0.5 g), and ethanol(290 mL).

(e) 5-Chloro-1,2,3-triazolo[4,5-c][1]benzazepine-4,10(1H,9H)-dione

To a solution of potassium t-butoxide (0.91 g, 8.1 mmol) in tetrahydrofuran (25 mL) at room temperature under nitrogen was added ethyl 4(6-chloro-2-aminobenzoyl)-1H-1,2,3-triazole-5-carboxylate (0.7823 g, 2.7 mmol) in tetrahydrofuran (25 mL). The reaction mixture was stirred for 2 hours and then was quenched with acetic acid (2 mL). The pH of the reaction mixture was adjusted to about 2 by the addition of concentrated hydrochloric acid and a solid formed which was collected by filtration (the acidic filtrate was saved for later use). The solid was dissolved in water and the aqueous layer was extracted with ethyl acetate. The organic layer was concentrated in vacuo and the residue thus obtained was combined wvith acidic filtrate. This mixture was then triturated with the aqueous layer and a brown solid formed which was collected by filtration and washed with water (2×10 mL) and hexane (2×10 mL). The solid was recrystallized from hot ethyl acetate to afford 0.059 g (9%) of the title compound as a light tan powder, m.p. >250° C.

EXAMPLE 51

Following conventional procedures well known in the pharmaceutical art it is contemplated that the following representative pharmaceutical dosage forms containing a compound of formula I can be prepared.

| (a) Tablet | |
|---|---|
| | mg/tablet |
| Compound of Formula I | 50.0 |
| Mannitol. USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

| (b) Capsule | |
|---|---|
| | mg/capsule |
| Compound of Formula I | 10.0 |
| Mannitol, USP | 488.5 |
| Croscarmellose sodium | 15.0 |
| Magnesium stearate | 1.5 |

(c) Injection

A sterile aqueous solution for intravenous administration may be prepared by dissolving a compound of Formula I in distilled water containing hydroxypropylmethylcellulose (0.5% by weight) and Tween 80 (0.1% by weight).

Representative examples of the compounds of the invention have been found to possess valuable pharmacological properties. In particular, they have been found to function as antagonists of the effects which excitatory amino acids, such as glutamate, have upon the NMDA receptor complex. The compounds of the invention are thus useful in the treatment of neurological disorders, i.e., strokes and/or other neurodegenerative disorders such as hypoglycemia cerebral palsy, transient cerebral ischemic attack, perinatal asphyxia epilepsy, psychosis, Huntington's chorea, arnotrophic lateral sclerosis, Alzheimer's disease, Parkinson's disease, Olivopontocerbellar atrophy, viral-induced neurodegeneration such as in acquired immunodeficiency syndrome and its associated dementia, anoxia such as from drowning, spinal cord and brain trauma, poisoning by exogenous neurotoxins, and chronic pain, for the prevention of drug and alcohol withdrawal symptoms and for the inhibition of tolerance and dependence to opiate analgesics.

The compounds of the invention are particularly useful in reducing neurological degeneration such as can be induced by stroke and the associated functional impairment which can result.

Treatment using a compound of the invention can be remedial or therapeutic as by administering a compound of the instant invention following an ischemic event to mitigate the effects of that event. Treatment can also be prophylactic or prospective by administering a compound of the instant invention in anticipation that an ischemic event may occur, for example in a patient who is prone to stroke.

The pharmacological properties of representative examples of the compounds of the invention were demonstrated by one or more of the following conventional in vitro and in vivo biological test procedures.

In Vitro Procedures

[$^3$H]-glycine Binding Assay

In the [$^3$H]-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000×g, 10 minutes), the supernatant is pelleted (20,000×g, 20 minutes) resuspended in double-distilled water. The suspension was centrifuged for 20 minutes at 8,000×g. The resulting supernatant and buffy coat are washed twice (48,000×g, 10 minutes, resuspension in double-deionized water). The final pellet is quickly frozen (dry ice/ethanol bath) under double-deionized water and stored at −70° C.

On the day of the experiment, thawed synaptic membranes are homogenized with a Brinkmann Polytron (TM, Brinkmann Instruments, Westbury, N.Y.) tissue homogenizer in 50 mM tris(hydroxymethyl)aminomethane citrate, pH 7.1. The membranes are incubated with 0.04% Sufact-AMPS X100 (TM, Pierce, Rockford, Ill.) in buffer for 20 minutes at 37° C. and washed six times by centrifugation (48,000×g, 10 minutes) and resuspended in buffer. The final pellet is homogenized at 200 mg wet weight/mL of the buffer for the binding assay.

For [$^3$H]-glycine binding at the N-methyl-D-aspartate receptor, 20 nM [$^3$H]-glycine (40–60 Ci/mmol, New England Nuclear, Boston, Mass.) is incubated with the membranes suspended in 50 mM tris(hydroxymethyl) aminomethane citrate, pH 7.1 for 30 minutes at 4° C. Glycine, 1mM, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GFB from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data.

The compounds of Examples 1(e), 2–19, 20(c), 21 (c), 22(c), 23(e), 24, 25(g), 26–47, 48(d), 49(e) and 50(e) were tested in the [$^3$H-glycine binding assay and were found to possess $IC_{50}$ values in the range of about 0.01 $\mu$M to about 100 $\mu$M. For example, the compounds of Examples 18, 27 and 28 were found to possess $IC_{50}$ values, respectively of 0.064 $\mu$M, 0.229 $\mu$M and 0.027 $\mu$M.

In Vivo Procedures

Gerbil Ischemic Model

Adult female Mongolian gerbils (50–70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped, gross behavioral observations along with motor activity are recorded for 2 hours on the first (24 hours) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undamaged, normal

1=slight damage (up to 25%)—restricted to CA1 subiculum border

2=moderate damage (up to 50%)—obvious damage, restricted to less than half of CA1 field 3=marked damage (up to 75%)—involving greater than half of CA1 field 4=damage extending beyond CA1 field Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxcon-Rank Sum test. The results can be reported as the percentage of neuroprotection afforded by a particular dose is and dosing regimen.

Representative test results for the compounds of the instant invention in the gerbil ischemic model are illustrated by the compound of Example 48(d) which was found to provide 77% neuroprotection when administered intraperitoneally (ip) twice (pre- and post-occlusion) at a dose of 20 mg/kg body weight.

Rat Middle Cerebral Artery Test

Male SHR rats weight 280–320 g are used for these studies. The method used for permanent middle cerebral artery (MCA) occlusion is as described by Brint et al (1988). Briefly, focal ischemia is produced by occluding first the left common carotid artery and then the left middle cerebral artery just superior to the rhinal fissure. Following occlusions, drugs are administered intravenously via jugular catheter. Twenty-four hours after MCA/common carotid artery occlusion, the animals are sacrificed and their brains quickly removed. Coronal sections of 1 mm thickness are cut using a vibratome and stained with 2,3,5-triphenyl-2H-tetrazolium chloride (TTC) dye. Following staining, necrotic tissue is readily distinguished from the intact brain and the area of infarcted cortex can be traced on an image analyzer. The infarct volume for each section is quantified with an image analyzer, and the total infarct volume is calculated with a program that sums all interval volumes. See S. Brint et al. J. Cerebral Blood Flow 8:474–475 (1988). The statistical analysis of the difference between the volume of ischemic damage in the vehicle control and drug-treated animals is analyzed by Student's t-test. The results are expressed as the percent (%) change in infarct volume and are presented as the mean for animals.

Representative tests results for the compounds of the instant invention in the rat middle cerebral artery test are illustrated by the compound of Example 18 which was found to provide a −19% change in infarct volume when administered intraveneously at a dose of 10 mg/kg per hour over 4 hours.

Rat Red Nucleus Test

The purpose of this test is to determine the effects of intravenously administered is glycine antagonists on the NMDA- induced excitatory response of red nucleus cells. HA-966 (racemic) and CGP 37849 are reference agents that have been shown to be active in this test ($ID_{50}$s of 7.9 and 1.7 mg/kg iv, respectively).

The procedure for the red nucleus test is as follows. Rats are anesthetized with chloral hydrate (400 mg/kg ip) and the femoral vein is catheterized for iv drug administration. Five-barrel micropipettes are stereotaxically positioned in the red nucleus. Typically, three to four of the five barrels are filled as follows: the recording barrel with 2M potassium citrate, the current balancing barrel with 4M NaCl, the drug barrel with 25 mM NMDA, and another drug barrel with 2.5 mM quisqualic acid (QA is only used in selectivity studies). NMDA is iontophoretically applied with an ejection current that is adjusted depending on the sensitivity of each individual red nucleus cell. The NMDA is cycled on and off (usually 30–60 sec. on and 60–120 sec. off) and the firing rate of the cell during each period is recorded. Once the baseline firing rate of the cell has been established, the test drug is administered iv. The inhibitory effect of the drug on the NMDA-induced excitatory response of the red nucleus cell can then be both qualitatively and quantitatively evaluated from the recordings and the raw data accumulated and the results are expressed as an $ID_{50}$ value (The dose in mg/kg of the test drug which causes 50% inhibition).

Representative test results for the compounds of the instant invention in the rat red nucleus test are illustrated by the compounds of Examples 1(e), 8, 13, 17–19, 23(e), 26–28, 30, 32, 34, 36, 38–40, 42 and 47 which were found to possess $ID_{50}$ values in the range of about 3.0 mg/kg to about 100 mg/kg. For example, the compounds of Examples 18, 27 and 28 were found to possess $ID_{50}$ values of 3.5, 5.7 and 4.6 mg/kg respectively.

The compounds of the invention are generally administered to patients which include, but are not limited to, mammals such as, for example, man. It will also be apparent to those skilled in the art that a compound according to the invention can be coadministered with other therapeutic or prophylactic agents and/or medicaments that are not medically incompatible therewith.

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more pharmaceutically acceptable carriers, adjuvants, diluents or vehicles, for oral administration in solid or liquid form, parenteral administration, topical administration, rectal administration, or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such was water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

Preparations according to the invention for rectal administration include suppositories prepared by using suitable carriers, e.g., cacao butter, hardened oils, glycerides or saturated fatty acids and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf. In general, a compound of the instant invention is administered at a dose in the range of about 0.01 to about 100 mg/kg body weight.

What is claimed is:

1. A compound of the formula I

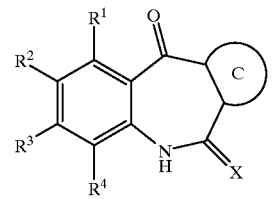

wherein:

X is O or S;

$R^1$, $R^2$, $R^3$ and $R^4$ are independently hydrogen, perfluorolower-alkyl, halogen, nitro or cyano;

C together with the carbon atoms to which it is attached forms a 5-membered aromatic heterocycle of the formula

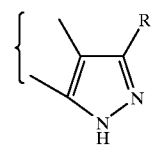

or tautomers thereof, wherein:

R is selected from cyano, formyl, phenylcarbonyl, phenyl, lower-alkylcarbonyl, perfluorolower-alkyl, lower-alkoxy-carbonyl-lower-alkyl, carboxy-lower-alkyl, and phenyl-lower-alkylcarbonyl; wherein said phenyl, phenyl-lower-alkyl, phenyl-lower-alkynyl, phenyl-lower-alkylamino, phenylcarbonyl or phenyl-loweralkylcarbonyl groups may optionally be substituted on the phenyl group thereof by one to three substituents, the same or different, selected from the group consisting of lower-alkyl, lower-alkoxy, halogen, hydroxy and trifluoromethyl; or R is —C(O)OR$^5$, where R$^5$ is selected from hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, and phenyl-lower-alkylamino; or R is —C(O)NR$^6$R$^7$, where R$^6$ and R$^7$ are independently selected from hydrogen, phenyl, phenyl-lower-alkyl, lower-alkoxy-lower-alkyl, hydroxylower-alkyl, lower-alkyl, lower-alkoxy, hydroxy, and cycloalkyl, or R$^6$ and R$^7$ together with the nitropen atom to which they are attached form a 5- or 6-membered non-aromatic heterocycle selected from morpholinyl, piperidinyl, piperazinyl, pyrrolidinyl and thiomorpholinyl:

or a pharmaceutically-acceptable acid-addition salt of basic members thereof; or a pharmaceutically-acceptable base-addition salt of acidic members thereof.

2. A compound according to claim 1 wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthiolower-alkyl, halo-lower-alkyl, trifluoromethyl-lower-alkyl, lower-alkyl-amino, cycloalkylamino, or phenyl-lower-alkylamino), —C(O)NR$^6$R$^7$ (wherein R$^6$ and R$^7$ are independently hydrogen, phenyl, phenyl-lower-alkyl, lower-alkoxy-lower-alkyl, lower-alkyl, lower-alkoxy, hydroxy or cycloalkyl, or R$^6$ and R$^7$ together with the nitrogen atom to which they are attached form a morpholinyl group), formyl, phenylcarbonyl, phenyl, lower-alkylcarbonyl, perfluorolower-alkyl, lower-alkoxycarbonyl-lower-alkyl, or carboxy-lower-alkyl; wherein said phenyl, phenyl-lower-alkyl, phenyl-lower-alkynyl, phenyl-lower-alkylamino or phenyl-carbonyl groups may optionally be substituted on the phenyl group thereof by one substituent selected from the group consisting of lower-alkyl, lower-alkoxy, halogen, hydroxy and trifluoromethyl.

3. A compound according to claim 2 wherein R is cyano, —C(O)OR$^5$ (wherein R$^5$ is hydrogen, lower-alkyl, lower-alkenyl, lower-alkynyl, cycloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkyl-amino, cycloalkylamino, or phenyl-lower-alkylamino), —C(O)NR$^6$R$^7$ (wherein R$^6$ and R$^7$ are independently hydrogen, phenyl, phenyl-lower-alkyl, lower-alkoxy-lower-alkyl, lower-alkyl, lower-alkoxy, or hydroxy, or R$^6$and R$^7$ together with the nitrogen atom to which they are attached form a morpholinyl group), formyl, phenylcarbonyl, phenyl, perfluorolower-alkyl, lower-alkoxycarbonyl-lower-alkyl, or carboxy-lower-alkyl.

4. A compound according to claim 3 wherein R$^1$, R$^2$, R$^3$ and R$^4$ are independently hydrogen or halogen.

5. A compound according to claim 4 wherein R is cyano, —C(O)OR$^5$ (wherein R$^5$ is hydrogen, methyl, ethyl, propyl, isopropyl, butyl, sec-butyl, isobutyl, 2-propenyl, 3-butenyl, 1-methyl-3-butenyl, 3-methyl-3-butenyl, 4-pentenyl, 3-butynyl, cyclopropylmethyl, phenyl, phenylmethyl, phenylethyl, phenylpropyl, 3-phenyl-2-propynyl, methylthioethyl, methylthiopropyl, chloroethyl, chloropropyl, 2,2,2-trifluoroethyl, isopropylamino, cyclohexylamino, tert-butyl-amino, phenylmethylamino), —C(O)NR$^6$R$^7$ (wherein R$^6$ and R$^7$ are independently hydrogen, phenylmethyl, phenyl, methoxyethyl, ethoxyethyl, propyl, methyl, methoxy, or hydroxy, or R$^6$ and R$^7$ together with the nitrogen atom to which they are attached form a morpholinyl group), formyl, phenylcarbonyl, phenyl, trifluoromethyl, tert-butoxycarbonylmethyl or carboxymethyl.

6. A compound according to claim 5 wherein one of R$^1$, R$^2$, R$^3$ or R$^4$ is chloro and the others are hydrogen.

7. A compound according to claim 5 selected from the group consisting of:
7-chloro-3-(carboxy)pyrazolo[3,4-c][1]benzazepine-4,10 (1H,9H)-dione,
7-chloro-3-cyanopyrazolo[3,4-c][1]benzazepine-4,10(1H, 9H)-dione,
7-chloro-3-trifluoromethylpyrazolo[3,4-c][1]benzazepine-4,10(1H,9H)-dione,
3-methoxycarbonyl-7-chloropyrazolo[3,4-c][1] benzazepine-4,10(1H,9H)-dione,
7-chloro-3-(ethoxycarbonyl)pyrazolo[3,4-c][1] benzazepine-4,10(1H,9H)-dione,
3-propoxycarbonyl-7-chloropyrazolo[3,4-c][1]benzepine-4,10(1H,9H)-dione,
7-chloro-3-(2-propenyloxycarbonyl)pyrazolo[3,4-c][1] benzazepin-4,10(1H,9H)-dione,
7-chloro-3-(isopropoxycarbonyl)pyrazolo[3,4-][1]-benzazepine-4,10(1H,9H)-dione,
3-butoxycarbonyl-7-chloropyrazolo[3,4-c][1]benzazepine-4,10(1H,9H)-dione,
3-(3-butenyloxycarbonyl)-7-chloropyrazolo[3,4-c][1] benzazepine-4,10(1H,9H)-dione, and
3-(3-butynyloxycarbonyl)-7-chloropyrazolo[3,4-c][1] benzazepine-4,10(1H,9H)-dione;

or a pharmaceutically acceptable salt thereof.

8. A method for the treatment of neurological disorders which comprises administering to a patient in need of such treatment an effective amount of a compound of the Formula I

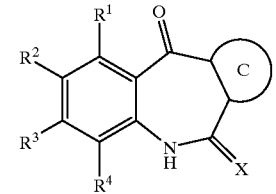

wherein:
X is O or S;
R$^1$, R$^2$, R$^3$ and R$^4$ are independently hydrogen, perfluorolower-alkyl, halogen, nitro or cyano; and
C together with the carbon atoms to which it is attached forms a 5-membered aromatic heterocycle selected from the group consisting of:

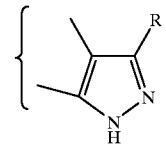 and 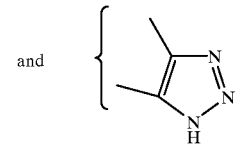

or tautomers thereof, wherein R is cyano, —C(O)OR$^5$ (wherein R$^5$ is hydrogen, lower-alkyl, lower-alkenyl, lower-alkynyl, cvcloalkyl-lower-alkyl, phenyl, phenyl-lower-alkyl, phenyl-lower-alkynyl, lower-alkylthio-lower-alkyl, halo-lower-alkyl, trifluoromethyl-lower-alkyl, lower-alkoxy-lower-alkyl, hydroxy-lower-alkyl, lower-alkylamino, cycloalkylamino, or phenyl-lower-alkylamino), —C(O)NR⁶R⁷ (wherein R⁶ and R⁷ are independently hydrogen, phenyl, phenyl-lower-alkyl lower-alkoxy-lower-alkyl, hydroxylower-alkyl, lower-alkyl, lower-alkoxy, hydroxy, or cycloalkyl, or R⁶ and R⁷ together with the nitrogen atom to which they are attached form a 5- or 6-membered non-aromatic heterocycle selected from the group consisting of morpholinyl, piperidinyl, piperazinyl, pyrrolidinyl and thiomorpholinyl), formyl, phenylcarbonyl, phenyl, lower-alkylcarbonyl, perfluorolower-alkyl, lower-alkoxycarbonyl-lower-alkyl, carboxy-lower-alkyl, or phenyl-lower-alkylcarbonyl; wherein said phenyl, phenyl-lower-alkyl, phenyl-lower-alkynyl, phenyl-lower-alkylamino, phenylcarbonyl or phenyl-lower-alkylcarbonyl groups may optionally be substituted on the phenyl group thereof by one to three substituents, the same or different, selected from the group consisting of lower-alkyl, lower-alkoxy, halogen, hydroxy and trifluoromethyl;

or a pharmaceutically acceptable acid-addition salt of basic members thereof, or a pharmaceutically acceptable base-addition salt of acidic members thereof.

9. A method according to claim 8 wherein C together with the carbon atoms to which it is attached forms a 5-membered aromatic heterocycle of the formula

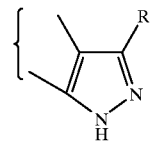

or tautomers thereof.

10. A method according to claim 9 wherein R is cyano, —C(O)OR⁵ (wherein R⁵ is hydrogen, lower-alkyl, lower-alkenyl, lower-alkynyl, cycloalkyl-lower-alkyl, phenyl, phenyl-lower-alkyl, phenyl-lower-alkynyl, lower-alkylthiolower-alkyl, halo-lower-alkyl, trifluoromethyl-lower-alkyl, lower-alkylamino, cycloalkylamino, or phenyl-lower-alkylamino), —C(O)NR⁶R⁷ (wherein R⁶ and R⁷ are independently hydrogen, phenyl, phenyl-lower-alkyl, lower-alkoxy-lower-alkyl, lower-alkyl lower-alkoxy, hydroxy or cycloalkyl, or R⁶ and R⁷ together with the nitrogen atom to which they are attached form a morpholinyl group), formyl, phenylcarbonyl, phenyl, lower-alkyl-carbonyl, perfluorolower-alkyl, lower-alkoxycarbonyl-lower-alkyl, or carboxy-lower-alkyl; wherein said phenyl, phenyl-lower-alkyl, phenyl-lower-alkynyl, phenyl-lower-alkylamino or phenylcarbonyl groups may optionally be substituted on the phenyl group thereof by one substituent selected from the group consisting of lower-alkyl, lower-alkoxy, halogen, hydroxy and trifluoromethyl.

11. A method according to claim 10 wherein R is cyano, —C(O)OR⁵ (wherein R⁵ is hydrogen, lower-alkyl, lower-alkenyl, lower-alkynyl, cycloalkyl-lower-alkyl, phenyl, phenyl-lower-alkyl, phenyl-lower-alkynyl, lower-alkyl-thiolower-alkyl, halo-lower-alkyl, trifluoromethyl-lower-alkyl, lower-alkylamino, cycloalkylarnino, or phenyl-lower-alkylamino), —C(O)NR⁶R⁷ (wherein R⁶ and R⁷ are independently hydrogen, phenyl, phenyl-lower-alkyl, lower-alkoxy-lower-alkyl, lower-alkyl, lower-alkoxy, or hydroxy, or R⁶ and R⁷ together with the nitrogen atom to which they are attached form a morpholinyl group), formyl, phenylcarbonyl, phenyl, perfluorolower-alkyl, lower-alkoxycarbonyl-lower-alkyl, or carboxy-lower-alkyl.

12. A method according to claim 11 wherein R¹, R², R³ and R⁴ are independently hydrogen or halogen.

13. A method according to claim 12 wherein R is cyano, —C(O)OR⁵ (wherein R⁵ is hydrogen, methyl, ethyl, propyl, isopropyl, butyl, sec-butyl, isobutyl, 2-propenyl, 3-butenyl, 1-methyl-3-butenyl, 3-methyl-3-butenyl, 4-pentenyl, 3-butynyl, cyclopropylmethyl, phenyl, phenylmethyl, phenylethyl, phenylpropyl, 3-phenyl-2-propynyl, methylthioethyl, methylthiopropyl, chloroethyl, chloropropyl, 2,2,2-trifluoroethyl, isopropylamino, cyclohexylanmino, tert-butylamino, phenylmethylamino), —C(O)NR⁶R⁷ (wherein R⁶ and R⁷ are independently hydrogen, phenylmethyl, phenyl, methoxyethyl, ethoxyethyl, propyl. methyl, methoxy, or hydroxy, or R⁶ and R⁷ together with the nitrogen atom to which they are attached form a morpholinyl group), formyl, phenylcarbonyl, phenyl, trifluoromethyl, tert-butoxycarbonylmethyl or carboxymethyl.

14. A method according to claim 13 wherein one of R¹, R², R³ or R⁴ is chloro and the others are hydrogen.

15. A method according to claim 14 wherein the compound is selected from the group consisting of
7-chloro-3-(carboxy)pyrazolo[3,4-c][1]benzazepine-4,10(1H,9H)-dione,
7-chloro-3-cyanopyrazolo[3,4-c][1]benzazepine-4,10(1H,9H)-dione,
7-chloro-3-trifluoromethylpyrazolo[3,4-c][1]benzazepine-4,10(1H,9H)-dione,
3-methoxycarbonyl-7-chloropyrazolo[3,4-c][1]benzazepine-4,10(1H,9H)-dione,
7-chloro-3-(ethoxycarbonyl)pyrazolo[3,4-c][1]benzazepine-4,10(1H,9H)-dione,
3-propoxycarbonyl-7-chloropyrazolo[3,4-c][1]benzazepine-4,10(1H,9H)-dione,
7-chloro-3-(2-propenyloxycarbonyl)pyrazolo[3,4-c]1]benzazepine-4,10(1H,9H)-dione,
7-chloro-3-(isopropoxycarbonyl)pyrazolo[3,4-c][1]benzazepine-4,10(1H,9H)-dione,
3-butoxycarbonyl-7-chloropyrazolo[3,4-c][1]benzazepine-4,10(1H,9H)-dione,
3-(3-butenyloxycarbonyl)-7-chloropyrazolo[3,4-c][1]benzazepine-4,10(1H,9H)-dione, and
3-(3-butynyloxycarbonyl)-7-chloropyrazolo[3,4-c[1]benzazepine-4,10(1H,9H)-dione;

or a pharmaceutically acceptable salt thereof.

16. A method according to claim 8 wherein C together with the carbon atoms to which it is attached forms a 5-membered aromatic heterocycle of the formula

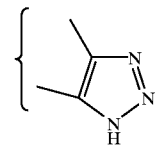

or tautomers thereof.

17. A method according to claim 16 wherein R¹, R², R³ and R⁴ are independently hydrogen or halogen.

18. A method according to claim 17 wherein one of R¹, R², R³ or R⁴ is chloro and the others are hydrogen.

19. A method according to claim 18 wherein the compound is selected from the group consisting of:
7-chloro-1,2,3-triazolo[4,5-c][1]benzazepine-4,10(1H,9H)-dione;

6-chloro-1,2,3-triazolo[4,5-c]1]benzazepine-4,10(1H,9H)-dione; and 5-chloro-1,2,3-triazolo[4,5-c][1]benzazepine-4,10(1H,9H)-dione;

or a pharmaceutically acceptable salt thereof.

20. A method according to claim 8 wherein said neurological disorder is stroke.

21. A pharmaceutical composition which comprises a compound according to claim 1, together with a pharmaceutically acceptable carrier, adjuvant, diluent or vehicle.

22. A pharmaceutical composition which comprises a compound according to anyone of claims 1–7 together with a pharmaceutically acceptable carrier, adjuvant, diluent or vehicle.

23. A process for preparing a compound according to claim 1 which comprises:

(1) treating a compound of the Formula II

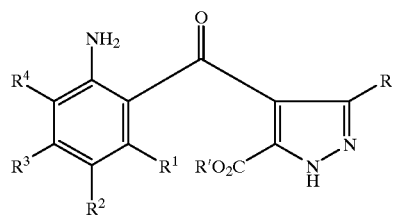

wherein R' is lower-alkyl, with an ammonium salt, 2-hydroxy-pyridine, or a base to prepare a corresponding compound of the formula I wherein C is a pyrazole ring.

* * * * *